United States Patent
Dupau et al.

(10) Patent No.: US 11,858,948 B2
(45) Date of Patent: Jan. 2, 2024

(54) HYDROGENATION OF CARBONYLS WITH TETRADENTATE PNNP LIGAND RUTHENIUM COMPLEXES

(71) Applicant: Firmenich SA, Satigny (CH)

(72) Inventors: Philippe Dupau, Satigny (CH); Lucia Bonomo, Satigny (CH); Laurent Kermorvan, Satigny (CH); Murielle Haldimann Sanchez, Satigny (CH)

(73) Assignee: FIRMENICH SA, Meyrin (CH)

( * ) Notice: Subject to any disclaimer, the term of this patent is extended or adjusted under 35 U.S.C. 154(b) by 259 days.

(21) Appl. No.: 16/766,543

(22) PCT Filed: Mar. 12, 2019

(86) PCT No.: PCT/EP2019/056139
§ 371 (c)(1),
(2) Date: May 22, 2020

(87) PCT Pub. No.: WO2019/175158
PCT Pub. Date: Sep. 19, 2019

(65) Prior Publication Data
US 2020/0399299 A1    Dec. 24, 2020

(30) Foreign Application Priority Data

Mar. 16, 2018 (EP) .................................. 18162243

(51) Int. Cl.
| | | |
|---|---|---|
| C07F 9/58 | (2006.01) | |
| C07F 15/00 | (2006.01) | |
| C07C 29/149 | (2006.01) | |
| B01J 31/24 | (2006.01) | |
| B01J 31/18 | (2006.01) | |
| C07B 35/00 | (2006.01) | |
| C07D 307/92 | (2006.01) | |

(52) U.S. Cl.
CPC ......... *C07F 15/0053* (2013.01); *B01J 31/189* (2013.01); *B01J 31/2409* (2013.01); *C07B 35/00* (2013.01); *C07D 307/92* (2013.01); *C07F 9/58* (2013.01); *B01J 2231/641* (2013.01); *B01J 2531/004* (2013.01); *B01J 2531/821* (2013.01); *C07C 29/149* (2013.01)

(58) Field of Classification Search
CPC ........ C07F 9/58; C07F 15/003; C07C 29/149; B01J 31/2409; B01J 31/189
See application file for complete search history.

(56) References Cited

FOREIGN PATENT DOCUMENTS

| | | |
|---|---|---|
| CN | 103709196 B | 8/2016 |
| WO | 2006106484 A1 | 10/2006 |
| WO | 2013023307 A1 | 2/2013 |

OTHER PUBLICATIONS

Wang et al., "New Ruthenium Complexes Based on Tetradentate Bipyridine Ligands for Catalytic Hydrogenation of Esters", Chemistry an Asian Journal, Aug. 5, 2016, pp. 2103-2106, 11(15).
DU et al. "Base-Metal-Catalyzed Regiodivergent Alkene Hydrosilylations" Angew. Chem. Int. Ed. 2016, 55, 6671-6675.
Numao et al.: "Improved Prediction of the Presence of Gleason Grade 4/5 Component by 3-Dimensional 26-Core Prostate Biopsy," European Urology Supplmen, Elsevier BV, NL, vol. 5, No. 2, Apr. 1, 2006, p. 313.
Tan et al.: "Highly Efficient Tetradentate Ruthenium Catalyst for Ester Reduction: Specifically for Hydrogenation of Fatty Acid Esters," Organic Letters 2015, 17(3), pp. 454-457.
International Search Report for PCT/EP2019/056139, dated Jun. 24, 2019, 3 pages.

*Primary Examiner* — Sikarl A Witherspoon
(74) *Attorney, Agent, or Firm* — Armstrong Teasdale LLP

(57) ABSTRACT

Described herein are catalytic hydrogenation processes, using Ru complexes with tetradentate ligands of formula L in hydrogenation processes for the reduction of ketone, aldehyde, ester, or lactone into the corresponding alcohol or diol respectively. These processes use a ruthenium complex of formula (1) as defined herein.

15 Claims, No Drawings

HYDROGENATION OF CARBONYLS WITH TETRADENTATE PNNP LIGAND RUTHENIUM COMPLEXES

CROSS-REFERENCE TO RELATED APPLICATIONS

This application is a U.S. National Phase Application of PCT/EP2019/056139, filed Mar. 12, 2019, which claims the benefit of priority to European Patent Application No. 18162243.2, filed Mar. 16, 2018, the entire contents of which are hereby incorporated by reference herein.

TECHNICAL FIELD

The present invention relates to the field of catalytic hydrogenation and, more particularly, to the use of Ru complex with tetradentate ligand of formula (L), in hydrogenation processes for the reduction of ketone, aldehyde, ester or lactone into the corresponding alcohol or diol respectively.

BACKGROUND

Reduction of a carbonyl functional group such as an aldehyde, a ketone or an ester functional group to the corresponding alcohol is one of the fundamental reactions in organic chemistry, and is used in a large number of chemical processes. In general, two main types of processes are known to achieve such a transformation. Such types of processes are the following:

a) hydride processes, in which a silyl or metal hydride salt, such as $LiAlH_4$, is used;
b) hydrogenation processes, in which molecular hydrogen is used.

From a practical point of view, hydrogenation processes are more attractive as they can be run using small amounts of catalyst (typically 10 to 1000 ppm relative to the substrate) and in the presence of small quantities or even in the absence of solvent. Furthermore, hydrogenation processes do not require the use of highly reactive and expensive hydrides, and do not produce important amounts of aqueous waste.

One of the mandatory and characterizing elements of hydrogenation processes is the catalyst or the catalytic system which is used to activate the molecular hydrogen in view of the reduction. The development of useful catalysts or catalytic systems for the hydrogenation of an ester functional group represents still an important need in chemistry.

The first hydrogenation conditions reported were performed under harsh conditions, i.e. high temperature and pressure. An improvement of the efficiency of esters hydrogenation has been reported in WO2006106484, WO2013023307 and more recently in Org. Lett., 2015, 17 (3), 454-457 or in CN103709196 wherein catalysts or catalytic systems comprising PNNP ligand or PNN ligand to perform such reductions have been disclosed. However there is still a need to improve the catalytic activity in such a reduction.

The present invention provides a solution to the above problem by performing said difficult hydrogenation of carbonyl group such an ester by using a novel PNNP ligand never reported in the literature so far.

SUMMARY OF THE INVENTION

Surprisingly, it has now been discovered that a catalyst comprising a tetradentate ligand as described in the present invention has a higher catalytic activity and is particularly efficient for the hydrogenation in the presence of a base of a carbonyl group such as ester or ketone group. The hydrogenation using said catalyst allows obtaining the desired alcohol more rapidly than by using catalyst reported in the prior arts.

So, a first object of the present invention is a process for the reduction by hydrogenation, using molecular $H_2$, of a $C_3$-$C_{70}$ substrate containing one or two ketones, aldehydes, esters, or lactones functional groups into the corresponding alcohol, or diol, characterized in that said process is carried out in the presence of a base and at least one catalyst or pre-catalyst containing Ruthenium and a tetradentate ligand of formula

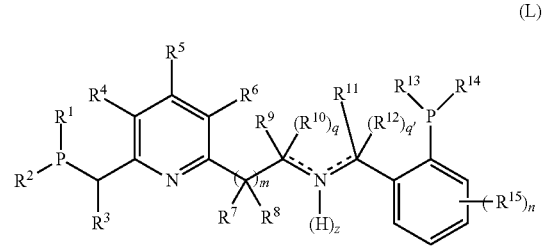

(L)

wherein one dotted line indicates a single bond and the other dotted line a single or a double bond, z is 1 when both dotted lines is a single bond or is 0 when one dotted line is a double bond and the other a single bond;
m is 0 or 1; n is a integer between 0 and 4;
q is 0 when the dotted line between N and $C(R^9)(R^{10})$ indicates a double bond or is 1 when the dotted line between N and $C(R^9)(R^{10})$ indicates a single bond;
q' is 0 when the dotted line between N and $C(R^{11})(R^{12})$ indicates a double bond or is 1 when the dotted line between N and $C(R^{11})(R^{12})$ indicates a single bond;
$R^1$ and $R^2$, when taken separately, represent, simultaneously or independently, a linear $C_1$ to $C_8$ alkyl group optionally substituted, a linear $C_2$ to $C_8$ alkenyl group optionally substituted, a branched or cyclic $C_3$ to $C_8$ alkyl or alkenyl group optionally substituted, a $C_6$ to $C_{10}$ aromatic group optionally substituted, or an $OR^{1'}$ or $NR^{1'}R^{2'}$ group, $R^{1'}$ and $R^{2'}$ being a $C_1$ to $C_8$ alkyl group or a $C_2$ to $C_8$ alkenyl group; or $R^1$ and $R^2$, when taken together, form a saturated or unsaturated ring optionally substituted, having 4 to 10 atoms and including the phosphorus atom to which said $R^1$ and $R^2$ groups are bonded;
$R^3$, $R^4$, $R^5$, $R^6$, $R^7$, $R^8$, $R^9$, $R^{10}$, $R^{11}$ and $R^{12}$, taken separately, represent, simultaneously or independently, a hydrogen atom, a $C_1$-$C_{10}$ linear alkyl group optionally substituted, a $C_2$-$C_{10}$ linear alkenyl group optionally substituted, a $C_3$-$C_{10}$ branched or cyclic alkyl or alkenyl group optionally substituted or a $C_6$ to $C_{10}$ aromatic group optionally substituted; or $R^3$ and $R^4$ and/or $R^4$ and $R^5$ and/or $R^5$ and $R^6$ and/or $R^6$ and $R^7$ and/or $R^7$ and $R^8$ and/or $R^8$ and $R^9$ and/or $R^9$ and $R^{10}$ and/or $R^{10}$ and/or $R^{11}$ and $R^{12}$, when taken together, form a saturated or unsaturated ring optionally substituted, having 4 to 10 atoms;
$R^{13}$ and $R^{14}$ when taken separately, represent, simultaneously or independently, a $C_6$ to $C_{10}$ aromatic group optionally substituted or an $OR^{1'}$ or $NR^{1'}R^{2'}$ group wherein $R^{1'}$ and
$R^{2'}$ is a $C_1$ to $C_8$ alkyl group or a $C_2$ to $C_8$ alkenyl group; and $R^{15}$ when taken separately, represent, simultaneously or independently, a hydrogen atom, a halogen atom, a linear $C_1$ to $C_8$ alkyl group optionally substituted, a linear $C_2$ to $C_8$ alkenyl group optionally substituted, a branched or cyclic $C_3$ to $C_8$ alkyl or alkenyl group optionally substituted, or a halo- or perhalo-hydrocarbon, CN, $SO_3R^{3'}$, $SO_2R^{3'}$, $NO_2$, $OR^{3'}$ or $CONR^{3'}R^{4'}$ group, $R^{3'}$ and $R^{4'}$, independently from each other, being a hydrogen atom or a $C_1$ to $C_8$ alkyl group or a $C_2$ to $C_8$ alkenyl group; two adjacent $R^{15}$ groups can be bonded together to form a $C_5$ to $C_{10}$ ring optionally substituted;

the optional substituents of $R^1$ to $R^{15}$ groups are one or two halogen atoms, $C_1$ to $C_{10}$ alkoxy, polyalkyleneglycols, halo- or perhalo-hydrocarbon, COOR, or R groups, wherein R is a $C_1$ to $C_6$ alkyl, or a $C_5$ to $C_{12}$ cycloalkyl, aralkyl (such as benzyl, phenethyl etc.) or aromatic group, the latter being also optionally substituted by one, two or three halogen atoms or $C_1$-$C_8$ alkyl, alkoxy, nitro, sulfonates, halo- or perhalo-hydrocarbon or ester groups.

A second object of the invention is a ligand of formula

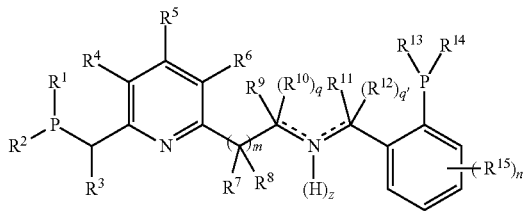

(L)

wherein m, n, q, q' z, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ have the same meaning as above.

A last object of the invention is a complex of formula (1), as defined above.

DESCRIPTION OF THE INVENTION

The invention relates to a novel and very efficient catalyst to be used in the very challenging hydrogenation, in particular for the hydrogenation of esters, hindered ketones or thermo sensitive ketones.

So, a first object of the present invention is a process for the reduction by hydrogenation, using molecular $H_2$, of a $C_3$-$C_{70}$ substrate containing one or two ketones, aldehydes, esters, or lactones functional groups into the corresponding alcohol, or diol, characterized in that said process is carried out in the presence of a base and at least one catalyst or pre-catalyst containing a ruthenium and a tetradentate ligand of formula

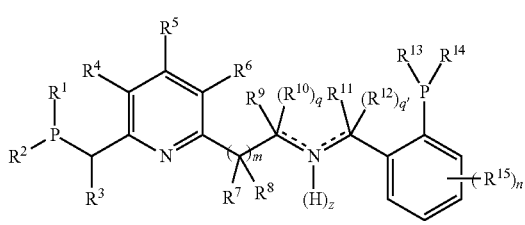

(L)

wherein one dotted line indicates a single bond and the other dotted line a single or a double bond, z is 1 when both dotted lines is a single bond (i.e. the nitrogen atom belongs to an amino group) or is 0 when one dotted line is a double bond and the other a single bond (i.e. the nitrogen atom belongs to an imino group);

m is 0 or 1; n is a integer between 0 and 4;

q is 0 when the dotted line between N and $C(R^9)(R^{10})$ indicates a double bond or is 1 when the dotted line between N and $C(R^9)(R^{10})$ indicates a single bond;

q' is 0 when the dotted line between N and $C(R^{11})(R^{12})$ indicates a double bond or is 1 when the dotted line between N and $C(R^{11})(R^{12})$ indicates a single bond;

$R^1$ and $R^2$, when taken separately, represent, simultaneously or independently, a linear $C_1$ to $C_8$ alkyl group optionally substituted, a linear $C_2$ to $C_8$ alkenyl group optionally substituted, a linear, branched or cyclic $C_3$ to $C_8$ alkyl or alkenyl group optionally substituted, a $C_6$ to $C_{10}$ aromatic group optionally substituted, or an $OR^{1'}$ or $NR^{1'}R^{2'}$ group, $R^{1'}$ and $R^{2'}$ being a $C_1$ to $C_8$ alkyl group or a $C_2$ to $C_8$ alkenyl group; or $R^1$ and $R^2$, when taken together, form a saturated or unsaturated ring optionally substituted, having 4 to 10 atoms and including the phosphorus atom to which said $R^1$ and $R^2$ groups are bonded;

$R^3$, $R^4$, $R^5$, $R^6$, $R^7$, $R^8$, $R^9$, $R^{10}$, $R^{11}$ and $R^{12}$, taken separately, represent, simultaneously or independently, a hydrogen atom, a $C_1$-$C_{10}$ linear alkyl group optionally substituted, a $C_2$-$C_{10}$ linear alkenyl group optionally substituted, a $C_3$-$C_{10}$ linear, branched or cyclic alkyl or alkenyl group optionally substituted or a $C_6$ to $C_{10}$ aromatic group optionally substituted;

or $R^3$ and $R^4$ and/or $R^4$ and $R^5$ and/or $R^5$ and $R^6$ and/or $R^6$ and $R^7$ and/or $R^7$ and $R^8$ and/or $R^8$ and $R^9$ and/or $R^9$ and $R^{10}$ and/or $R^9$ and $R^{11}$ and/or $R^{11}$ and $R^{12}$, when taken together, form a saturated or unsaturated ring optionally substituted, having 4 to 10 atoms;

$R^{13}$ and $R^{14}$ when taken separately, represent, simultaneously or independently, a linear $C_1$ to $C_8$ alkyl group optionally substituted, a linear $C_2$ to $C_8$ alkenyl group optionally substituted, a linear, branched or cyclic $C_3$ to $C_8$ alkyl or alkenyl group optionally substituted, a $C_6$ to $C_{10}$ aromatic group optionally substituted, or an $OR^{1'}$ or $NR^{1'}R^{2'}$ group, $R^{1'}$ and $R^{2'}$ being a $C_1$ to $C_8$ alkyl group or a $C_2$ to $C_8$ alkenyl group; or $R^{13}$ and $R^{14}$, when taken together, form a saturated or unsaturated ring optionally substituted, having 4 to 10 atoms and including the phosphorus atom to which said $R^{13}$ and $R^{14}$ groups are bonded; and $R^{15}$, when taken separately, represent, simultaneously or independently, a hydrogen atom, a halogen atom, a linear $C_1$ to $C_8$ alkyl group optionally substituted, a linear $C_2$ to $C_8$ alkenyl group optionally substituted, a linear, branched or cyclic $C_3$ to $C_8$ alkyl or alkenyl group optionally substituted, or a halo- or perhalo-hydrocarbon, CN, $SO_3R^{3'}$, $SO_2R^{3'}$, $NO_2$, $OR^{3'}$, or $CONR^{3'}R^{4'}$ group, $R^{3'}$ and $R^{4'}$, independently from each other, being a hydrogen atom or a $C_1$ to $C_8$ alkyl group or a $C_2$ to $C_8$ alkenyl group; two adjacent $R^{15}$ groups can be bonded together to form a $C_5$ to $C_{10}$ ring optionally substituted.

$R^{15}$ may be, relative to the phosphine substituent, an ortho, a meta, a para substituent of the aromatic ring.

According to a particular embodiment of the invention, the substrate can be a compound of formula (I)

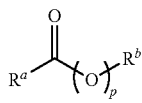

(I)

Wherein p is 0 or 1; when p is 1, $R^a$ and $R^b$ represent, simultaneously or independently, a linear, branched or cyclic $C_1$-$C_{30}$ aromatic, alkyl or alkenyl group, optionally substituted; or when p is 0, $R^a$ represents a linear, branched or cyclic $C_1$-$C_{30}$ aromatic, alkyl or alkenyl group, optionally substituted and $R^b$ represents a hydrogen atom, a linear, branched or cyclic $C_1$-$C_{30}$ aromatic, alkyl or alkenyl group, optionally substituted; or $R^a$ and $R^b$ are bonded together and form a $C_4$-$C_{20}$ saturated or unsaturated group, optionally substituted.

When p is 1, the corresponding alcohols (i.e (II-a) and (II-b)), or the corresponding diol (II'), of said substrate (I), are of formula

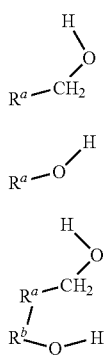

(II-a)

(II-b)

(II')

wherein $R^a$ and $R^b$ are defined as in formula (I).

A compound of formula (II) (i.e. II-a or II-b) will be obtained in the case where $R^a$ and $R^b$ are not bonded together, while a compound of formula (II') will be obtained in the case where $R^a$ and $R^b$ are bonded together.

When p is 0, the corresponding alcohols of said substrate (I) are of formula

(II-c)

wherein $R^a$ and $R^b$ are defined as in formula (I).

It is understood that by "a linear, branched or cyclic . . . aromatic, alkyl, or alkenyl group" it is meant that said $R^a$ or $R^b$ can be in the form of, e.g., a linear alkyl group or can also be in the form of a mixture of said type of groups, e.g. a specific $R^a$ may comprises a linear alkyl, a branched alkenyl, a (poly)cyclic alkyl and an aryl moiety, unless a specific limitation to only one type is mentioned. Similarly, in all the below embodiments of the invention when a group is mentioned as being in the form of more than one type of topology (e.g. linear, cyclic or branched) and/or unsaturation (e.g. alkyl, aromatic or alkenyl) it is meant also a group which may comprise moieties having any one of said topologies or unsaturations, as above explained.

According to a further embodiment of the invention, the substrate is a ketone, an aldehyde, an ester, or a lactone that will provide an alcohol or a diol, which is useful in the pharmaceutical, agrochemical or perfumery industry as final product or as an intermediate. Particularly preferred substrate is a ketone, an aldehyde, an ester, or a lactone that will provide an alcohol or diol, which is useful in the perfumery industry as final product or as an intermediate. Even a more particularly preferred substrate is an ester, or a lactone that will provide an alcohol or diol, which is useful in the perfumery industry as final product or as an intermediate.

A particular embodiment of the invention's process is shown in Scheme 1:

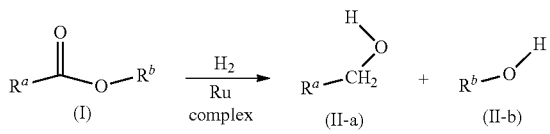

According to any one of the above embodiments of the invention, p is 0 or 1. Preferably p is 1.

According to any one of the above embodiments of the invention, the substrate is a $C_5$-$C_{30}$ compound of formula (I), and in particular one may cite those wherein $R^a$ and $R^b$ represent simultaneously or independently a linear $C_1$-$C_{30}$ alkyl group optionally substituted, a branched or cyclic $C_3$-$C_{30}$ alkyl or alkenyl group optionally substituted or a $C_5$-$C_{30}$ aromatic group optionally substituted; or $R^a$ and $R^b$ are bonded together and form a $C_4$-$C_{20}$ saturated or unsaturated linear, branched, mono-, di- or tri-cyclic group, optionally substituted.

According to a further embodiment of the invention the substrate is a $C_5$-$C_{20}$ compound of formula (I), wherein $R^a$ and $R^b$ represent simultaneously or independently a linear, branched or cyclic $C_5$-$C_{18}$ aromatic or alkyl group, optionally substituted, or a cyclic $C_5$-$C_{18}$ alkenyl group, optionally substituted; or $R^a$ and $R^b$ are bonded together and form a $C_4$-$C_{20}$ saturated or unsaturated linear, branched, mono-, di- or tri-cyclic group, optionally substituted.

Furthermore, according to a yet further embodiment, when $R^a$ and/or $R^b$ represent an alkenyl group then the carbon-carbon double bond is not terminal and is not conjugated.

Possible substituents of $R^a$ and $R^b$ are one, two or three halogen, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group, preferably a $C_1$ to $C_4$ linear or branched alkyl or alkenyl group. As other possible substituents one may also cite a group $COOR^c$, which can also be reduced to the corresponding alcohol during the invention's process, according to the molar amount of $H_2$ used, as well known by a person skilled in the art.

Non-limiting examples of substrates are alkyl cinnamates, sorbates or salycilates, alkyl esters of natural (fatty or not) acids, Sclareolide, spirolactones, allylic ester, di alkyl diesters, (un)substituted benzoic esters, and unsaturated esters such as 13-7 unsaturated esters. In particular, the substrate can be selected from the group consisting of sclareolide, $C_9$-$C_{15}$ spirolactones and $C_1$-$C_4$ alkyl esters of 4-methyl-6-(2,6,6-trimethyl-1-cyclohexen-1-yl)-3-hexenoic acid. One can also cite the di alkyl esters of 1,4-dicarboxylate-cyclohexane, the di $C_{1-5}$ alkyl esters of the $C_{2-10}$ alkanediyl-dicarboxylates, $C_{1-5}$ alkyl cyclopropanecarboxylates, mono-, di- or tri-methoxybenzoic esters.

The process of the invention is characterized by the use, as catalyst or pre-catalyst (hereinafter referred to as complexes unless specified otherwise), of a ruthenium complex as described above. The complex can be in the form of an ionic or neutral species.

According to an embodiment of the invention, the ruthenium complex can be of the general formula

[Ru(L)Y$_2$]  (1)

[Ru(L)(X)(Y)$_2$]  (2)

[Ru(L)(X)$_n$(Y)$_{2-n}$](Z)$_n$  (3)

wherein L represents a tetradentate ligand as defined above; and each Y represents, simultaneously or independently, CO, a hydrogen or halogen atom, a hydroxyl group, or a $C_1$-$C_6$ alkyl, alkenyl, alkoxy or carboxylic radical, or also a $BH_4$ or $AlH_4$ group;

X represents a $C_3$-$C_{30}$ mono-phosphine or a solvent.

Z represents a non-coordinated anion; and n is 0, 1 or 2.

In a particular embodiment of the invention, in formula (1), (2) or (3), each Y represents, simultaneously or independently, a hydrogen or chlorine atom, a hydroxy radical, a $C_1$ to $C_6$ alkoxy radical, such as a methoxy, ethoxy or isopropoxy radical, or a $C_1$ to $C_6$ acyloxy radical such as a $CH_3COO$, $CH_3CH_2COO$ or $(CH_3)_3CCOO$ radical. More preferably, each Y represents, simultaneously or independently, a hydrogen or chlorine atom, a methoxy, ethoxy or isopropoxy radical, or a $CH_3COO$, $CH_3CH_2COO$ or $(CH_3)_3CCOO$ radical.

In a particular embodiment of the invention, in formula (2), the tetradendate ligand L is partly coordinated to a metal; i.e. only 3 atoms are coordinated to the Metal. When complex of formula (2) is used, the complex of formula (1) is formed in situ under the reaction conditions.

In a particular embodiment of the invention, in formula (2) or (3), X represents a mono-phosphine of formula $PR^d_3$, wherein $R^d$ is a $C_1$-$C_{12}$ group, such as linear, branched or cyclic alkyl, alkoxy or aryloxy group optionally substituted, substituted or unsubstituted phenyl, diphenyl or naphthyl or di-naphthyl group. More particularly $R^d$ may represent a substituted or unsubstituted phenyl, diphenyl or naphthyl or di-naphthyl group. Possible substituents are those cited below for the various groups $R^1$ to $R^{15}$. Preferably, X is a triphenylphosphine.

In formula (3), X may also be a solvent, the term "solvent" has to be understood according to the usual meaning in the art and includes compounds used as diluent in the preparation of the complex or during the invention's process, non-limiting examples are dimethylsulfoxide, acetonitrile, dimethylformamide, an alcohol (e.g. an $C_1$-$C_4$ alcohol), or also THF, acetone, pyridine or a $C_3$-$C_8$ ester or the substrate of the invention's process.

In a particular embodiment of the invention, in formula (3), Z represents a halogen atom, a hydroxyl group, or a $C_1$-$C_6$ alkoxy, phenoxy or carboxylic radical.

The complex of formula (1) represents, in general for practical reasons, a preferred embodiment of the invention.

Possible substituents of the various groups $R^1$ to $R^{15}$ are one or two halogen atoms, $C_1$ to $C_{10}$ alkoxy, polyalkyleneglycols, halo- or perhalo-hydrocarbon, COOR, or R groups, wherein R is a $C_1$ to $C_6$ alkyl, or a $C_5$ to $C_{12}$ cycloalkyl, aralkyl (such as benzyl, phenethyl etc.) or aromatic group, the latter being also optionally substituted by one, two or three halogen atoms or $C_1$-$C_8$ alkyl, alkoxy, nitro, sulfonates, halo- or perhalo-hydrocarbon or ester groups. By "halo- or perhalo-hydrocarbon" it is meant groups such as $CF_3$ or $CClH_2$ for instance. Preferably, said substituents can be, and in particular when said groups are or contain phenyl groups, one or two halogen atoms, one or two $C_1$ to $C_5$ alkoxy or polyalkyleneglycols groups, COOR or R groups wherein R is a $C_1$ to $C_4$ alkyl, or a $C_{5-6}$ cycloalkyl, aralkyl or aromatic group, the latter being also optionally substituted as above defined. Alternatively, possible substituents of $R^3$, $R^4$, $R^5$, $R^6$, $R^7$, $R^8$, $R^9$, $R^{10}$, $R^{11}$ and $R^{12}$ are one or two halogen atoms or $R^{16}$ or $OR^{16}$ groups wherein $R^{16}$ being a $C_1$ to $C_6$ alkyl groups or a $C_1$ to $C_4$ alkyl groups.

According to a particular embodiment of the invention, m is 1. In other words, L can be a compound of formula

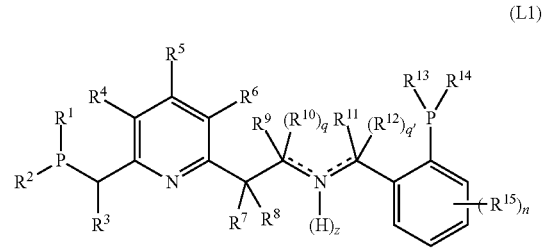
(L1)

wherein the dotted lines, z, n, q, q', $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ have the same meaning as above.

According to a particular embodiment of the invention, m is 0. In other words, L can be a compound of formula

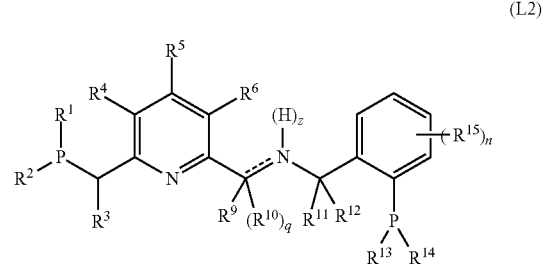
(L2)

Wherein the dotted line, z, n, q, $R^1$, $R^2$, $R^3$, $R^4$, $R^5$, $R^6$, $R^9$, $R^{10}$, $R^{11}$, $R^{12}$, $R^{13}$, $R^{14}$ and $R^{15}$ have the same meaning as above.

According to a particular embodiment of the invention, L can be a compound of formula

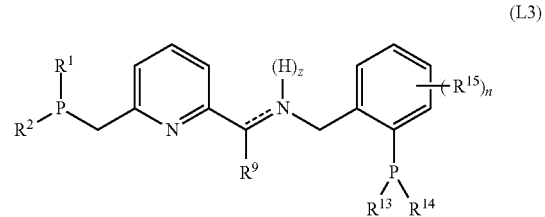
(L3)

wherein the dotted line, z, n, $R^1$, $R^2$, $R^9$, $R^{13}$, $R^{14}$ and $R^{15}$ have the same meaning as above.

According to a particular embodiment of the invention, L can be a compound of formula

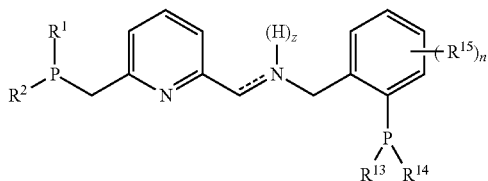

(L4)

wherein the dotted line, z, n, $R^1$, $R^2$, $R^{12}$, $R^{13}$, $R^{14}$ and $R^{15}$ have the same meaning as above.

According to any one of the above embodiments of the invention, $R^1$ and $R^2$ may represent, when taken separately, simultaneously or independently, a linear $C_1$ to $C_8$ alkyl group optionally substituted, a linear $C_2$ to $C_8$ alkenyl group optionally substituted, a branched or cyclic $C_3$ to $C_8$ alkyl or alkenyl group optionally substituted, a $C_6$ to $C_{10}$ aromatic group optionally substituted; or $R^1$ and $R^2$, when taken together, may form a saturated or unsaturated ring optionally substituted, having 4 to 10 atoms and including the phosphorus atom to which said $R^1$ and $R^2$ groups are bonded. Preferably, $R^1$ and $R^2$ may represent, when taken separately, simultaneously or independently, a linear $C_1$ to $C_6$ alkyl group optionally substituted, a branched or cyclic $C_3$ to $C_6$ alkyl group optionally substituted, a phenyl group optionally substituted; or $R^1$ and $R^2$, when taken together, may form a saturated or unsaturated ring optionally substituted, having 4, 5, 6 or 7 carbon atoms and including the phosphorus atom to which said $R^1$ and $R^2$ groups are bonded. Preferably, $R^1$ and $R^2$ may represent a linear $C_1$ to $C_6$ alkyl group optionally substituted, a branched or cyclic $C_3$ to $C_6$ alkyl group optionally substituted or a phenyl group optionally substituted. Preferably, $R^1$ and $R^2$ may represent a linear $C_1$ to $C_6$ alkyl group, a branched or cyclic $C_3$ to $C_6$ alkyl group or a phenyl group. Even more preferably, $R^1$ and $R^2$ may represent a cyclohexyl, a phenyl, a tert-butyl, an iso-propyl or an ethyl group. Even more preferably, $R^1$ and $R^2$ may represent a phenyl or a tert-butyl group.

According to any one of the above embodiments of the invention, $R^{13}$ and $R^{14}$, when taken separately, represent, simultaneously or independently, a $C_6$ to $C_{10}$ aromatic group optionally substituted or an $OR^{1'}$ or $NR^{1'}R^{2'}$ group wherein $R^{1'}$ and $R^{2'}$ is a $C_1$ to $C_8$ alkyl group or a $C_2$ to $C_8$ alkenyl group. Preferably, $R^{13}$ and $R^{14}$ may represent phenyl group optionally substituted. Even more preferably, $R^{13}$ and $R^{14}$ may represent phenyl group substituted with at least one halogen atom, halo- or perhalo-hydrocarbon or R group wherein R is a $C_1$ to $C_4$ alkyl, or a $C_{5-6}$ cycloalkyl, aralkyl or aromatic group, the latter being also optionally substituted as above defined.

According to any one of the above embodiments of the invention, $R^3$, $R^4$, $R^5$, $R^6$, $R^7$, $R^8$, $R^9$, $R^{10}$, $R^{11}$ and $R^{12}$, taken separately, represent, simultaneously or independently, a hydrogen atom, a $C_1$-$C_6$ linear alkyl group optionally substituted, a $C_2$-$C_6$ linear alkenyl group optionally substituted, a $C_3$-$C_6$ branched or cyclic alkyl or alkenyl group optionally substituted or a $C_6$ to $C_{10}$ aromatic group optionally substituted; or $R^4$ and $R^5$ and/or $R^5$ and $R^6$ and/or $R^8$ and $R^9$, when taken together, form a saturated or unsaturated ring optionally substituted, having 4 to 10 atoms; or $R^9$ and $R^{11}$, when taken together, form a saturated or unsaturated non aromatic ring optionally substituted, having 4 to 10 atoms. Preferably, $R^3$, $R^4$, $R^5$, $R^6$, $R^7$, $R^8$, $R^9$, $R^{10}$, $R^{11}$, and $R^{12}$, taken separately, may represent, simultaneously or independently, a hydrogen atom, a $C_1$-$C_4$ linear alkyl group optionally substituted, a $C_5$-$C_6$ branched or cyclic alkyl group optionally substituted or a phenyl group optionally substituted; $R^4$ and $R^5$ or $R^5$ and $R^6$ or $R^8$ and $R^9$, when taken together, form a saturated or unsaturated ring optionally substituted, having 4 to 7 carbon atoms. Preferably, $R^3$, $R^4$, $R^5$, $R^6$, $R^7$, $R^8$, $R^9$, $R^{11}$ and $R^{12}$ may represent a hydrogen atom, a methyl or a phenyl group. Even more preferably, $R^3$, $R^4$, $R^5$, $R^6$, $R^7$, $R^8$, $R^9$, $R^{11}$ and $R^{12}$ may represent a hydrogen atom According to any one of the above embodiments of the invention, n may be 0, 1 or 2. Preferably, n is 0 or 1. When n is 1, $R^{15}$ may be, relative to the phosphine substituent, a meta or a para substituent of the aromatic ring. Preferably, $R^{15}$ may be, relative to the phosphine substituent, a para substituent of the aromatic ring.

According to any one of the above embodiments of the invention, $R^{15}$, when taken separately, may represent, simultaneously or independently, a halogen atom, a linear $C_1$ to $C_4$ alkyl group optionally substituted, a linear $C_2$ to $C_5$ alkenyl group optionally substituted, a linear, branched or cyclic $C_3$ to $C_8$ alkyl or alkenyl group optionally substituted, or a halo- or perhalo-hydrocarbon group. Preferably, may represent, simultaneously or independently, a halogen atom, or a halo- or perhalo-hydrocarbon group such as $CF_3$.

Examples of suitable ligands includes, but are not limited to, 1-(6-((diphenylphosphaneyl)methyl)pyridin-2-yl)-N-(2-(diphenylphosphaneyl)phenyl)methanimine, 2-(diphenylphosphaneyl)-N-((6-((diphenylphosphaneyl)methyl)pyridin-2-yl)methyl)aniline, 2-(diphenylphosphaneyl)-N-(1-(6-((diphenylphosphaneyl)methyl)pyridin-2-yl)ethyl)aniline, 1-(6-((diphenylphosphaneyl)methyl)pyridin-2-yl)-N-(2-(diphenylphosphaneyl)phenyl)ethan-1-imine, 1-(6-((diphenylphosphaneyl)methyl)pyridin-2-yl)-N-(2-(diphenylphosphaneyl)phenyl)-1-phenylmethanimine, 2-(diphenylphosphaneyl)-N-((6-((diphenylphosphaneyl)methyl)pyridin-2-yl) (phenyl)methyl) aniline, 2-(diphenylphosphaneyl)-N-((6-((diphenylphosphaneyl)methyl)pyridin-2-yl)methyl)-5-(trifluoromethyl)aniline, N-(2-(diphenylphosphaneyl)-5-(trifluoromethyl)phenyl)-1-(6-((diphenylphosphaneyl)methyl)pyridin-2-yl)methanimine, N-(5-chloro-2-(diphenylphosphaneyl)phenyl)-1-(6-((diphenylphosphaneyl)methyl)pyridin-2-yl)methanimine, 5-chloro-2-(diphenylphosphaneyl)-N-((6-((diphenylphosphaneyl)methyl)pyridin-2-yl)methyl)aniline, 4-chloro-2-(diphenylphosphaneyl)-N-((6-((diphenylphosphaneyl)methyl)pyridin-2-yl)methyl)aniline, N-(4-chloro-2-(diphenylphosphaneyl)phenyl)-1-(6-((diphenylphosphaneyl)methyl)pyridin-2-yl)methanimine, N-(2-(diphenylphosphaneyl)-4-(trifluoromethyl)phenyl)-1-(6-((diphenylphosphaneyl)methyl)pyridin-2-yl)methanimine, 2-(diphenylphosphaneyl)-N-((6-((diphenylphosphaneyl)methyl)pyridin-2-yl)methyl)-4-(trifluoromethyl)aniline, N-((6-((diisopropylphosphaneyl)methyl)pyridin-2-yl)methyl)-2-(diphenylphosphaneyl)-4-(trifluoromethyl)aniline, 1-(6-((diisopropylphosphaneyl)methyl)pyridin-2-yl)-N-(2-(diphenylphosphaneyl)-4-(trifluoromethyl)phenyl)methanimine, N-(4-chloro-2-(diphenylphosphaneyl)phenyl)-1-(6-((diisopropylphosphaneyl)methyl)pyridin-2-yl)methanimine, 4-chloro-N-((6-((diisopropylphosphaneyl)methyl)pyridin-2-yl)methyl)-2-(diphenylphosphaneyl) aniline, 5-chloro-N-((6-((diisopropylphosphaneyl)methyl)pyridin-2-yl)methyl)-2-(diphenylphosphaneyl)aniline, N-(5-chloro-2-(diphenylphosphaneyl)phenyl)-1-(6-((diisopropylphosphaneyl)methyl)pyridin-2-yl)methanimine, 1-(6-((diisopropylphosphaneyl)methyl)pyridin-2-yl)-N-(2-(diphenylphosphaneyl)-5-(trifluoromethyl)phenyl)methanimine, ((6-((diisopropylphosphaneyl)methyl)pyridin-2-yl)methyl)-2-(diphenylphosphaneyl)-5-(trifluoromethyl)aniline, ((6-((di-tert-butylphosphaneyl)methyl)pyridin-2-yl)methyl)-2-(diphenylphosphaneyl)-5-(trifluoromethyl)aniline, 1-(6-((di-tert-butylphosphaneyl)methyl)pyridin-2-yl)-N-(2-(diphenylphosphaneyl)-5-(trifluoromethyl)phenyl)methanimine, N-(5-chloro-2-(diphenylphosphaneyl)phenyl)-1-(6-((di-tert-butylphosphaneyl)methyl)pyridin-2-yl)methanimine, 5-chloro-N-((6-((di-tert-butylphosphaneyl)methyl)pyridin-2-yl)methyl)-2-(diphenylphosphaneyl)aniline, N-(4-chloro-2-(diphenylphosphaneyl)phenyl)-1-(6-((di-tert-butylphosphaneyl)methyl)pyridin-2-yl)methanimine, 4-chloro-N-((6-((di-tert-butylphosphaneyl)methyl)pyridin-2-yl)methyl)-2-(diphenylphosphaneyl)aniline, N-((6-((di-tert-butylphosphaneyl)methyl)pyridin-2-yl)methyl)-2-(diphenylphosphaneyl)-4-(trifluoromethyl)aniline, 1-(6-((di-tert-butylphosphaneyl)methyl)pyridin-2-yl)-N-(2-(diphenylphosphaneyl)-4-(trifluoromethyl)phenyl)methanimine, 1-(6-((di-tert-butylphosphaneyl)methyl)pyridin-2-yl)-N-(2-(diphenylphosphaneyl)phenyl)ethan-1-imine, N-(1-(6-((di-tert-butylphosphaneyl)methyl)pyridin-2-yl)ethyl)-2-(diphenylphosphaneyl) aniline, N-((6-((di-tert-butylphosphaneyl)methyl)pyridin-2-yl) (phenyl)methyl)-2-(diphenylphosphaneyl)aniline, 1-(6-((di-tert-butylphosphaneyl)methyl)pyridin-2-yl)-N-(2-(diphenylphosphaneyl)phenyl)-1-phenylmethanimine, 1-(6-((di-tert-butylphosphaneyl)methyl)pyridin-2-yl)-N-(2-(diphenylphosphaneyl)phenyl)methanimine, N-((6-((di-tert-butylphosphaneyl)methyl)pyridin-2-yl)methyl)-2-(diphenylphosphaneyl) aniline, N-((6-((diisopropylphosphaneyl)methyl)pyridin-2-yl)methyl)-2-(diphenylphosphaneyl) aniline, 1-(6-((diisopropylphosphaneyl)methyl)pyridin-2-yl)-N-(2-(diphenylphosphaneyl)phenyl)methanimine, 1-(6-((diethylphosphaneyl)methyl)pyridin-2-yl)-N-(2-(diphenylphosphaneyl)phenyl)methanimine, N-((6-((diethylphosphaneyl)methyl)pyridin-2-yl)methyl)-2-(diphenylphosphaneyl) aniline, 1-(6-((dicyclohexylphosphaneyl)methyl)pyridin-2-yl)-N-(2-(diphenylphosphaneyl)phenyl)methanimine, N-((6-((dicyclohexylphosphaneyl)methyl)pyridin-2-yl)methyl)-2-(diphenylphosphaneyl) aniline, N-(2-(6-((diphenylphosphaneyl)methyl)pyridin-2-yl)ethyl)-1-(2-(diphenylphosphaneyl)phenyl)methanimine, N-(2-(diphenylphosphaneyl)benzyl)-2-(6-((diphenylphosphaneyl)methyl)pyridin-2-yl)ethan-1-amine, 2-(6-((di-tert-butylphosphaneyl)methyl)pyridin-2-yl)-N-(2-(diphenylphosphaneyl)benzyl)ethan-1-amine or N-(2-(6-((di-tert-butylphosphaneyl)methyl)pyridin-2-yl)ethyl)-1-(2-(diphenylphosphaneyl)phenyl)methanimine.

When the ligand is an imine, said ligand may be in a Z or E configuration, preferably in E.

The ligands described above can be obtained by applying standard methods which are well known in the state of the art and by the person skilled in the art. Therefore, their preparation does not require a specific description. For example one may revert to *Org. Lett.*, 2015, 17 (3), 454-457.

In general, the complexes of formula (1) can be prepared and isolated prior to their use in the process according to the general methods described in the literature. A method is described in the Example.

Moreover, the complexes can be prepared in situ, by several methods, in the hydrogenation medium, without isolation or purification, just before their use.

One of the possible procedures to advantageously prepare in situ a complex of the invention consists in reacting an appropriate Ru complex of formula [Ru("diene")("allyl")$_2$], wherein "diene" represents a cyclic or linear hydrocarbon containing two carbon-carbon double bonds, conjugated or not, such as for example 1,5-cyclooctadiene (COD) or norbornadiene, and "allyl" represents a linear or branched $C_3$ to $C_8$ hydrocarbon radical containing one carbon-carbon double bond such as methylallyl or allyl, with a non-coordinating acid such as HBF$_4$·Et$_2$O, and then treating the resulting solution with the required amount of a ligands L, such as defined previously, to give a solution of a catalyst according to formula (3). Furthermore, the mixture thus obtained can also be treated with a base in the presence of a primary or secondary alcohol. Furthermore, the complexes of formula (1) or (2) can be prepared by reacting an appropriate Ru complex such as, [Ru("diene")("allyl")$_2$], [RuCl$_2$(PPh$_3$)$_3$], [RuCl$_2$(COD)] or [RuCl$_2$(arene)]$_2$ with the required amount of a ligands L, such as defined previously (COD representing a cyclooctadiene and arene being e.g. a benzene or naphthalene).

It is also understood that the complex of the invention can also be obtained in situ from complexes which have a similar formula and which in presence of, for example an alcohol and a base, are converted into a invention's ruthenium complex, for example, from a complex wherein Y has other meaning.

To carry out the processes of the invention it is required also to use a base. Said base can be the substrate itself, if the latter is basic, a corresponding alcoholate or any base having preferentially a pK$_a$ above 11. According to a particular embodiment of the invention said base may have a pK$_a$ above 14. It is also understood that preferably said base does not reduce itself a substrate of formula (I). As non-limiting examples one may cite the following type of base: alcoholate, hydroxides, alkaline or alkaline-earth carbonates, phosphazenes, alkylamidines, alkylguanidine amides, basic alox, siliconates (i.e. silicium derivatives having SiO$^-$ or SiRO$^-$ groups), hydrides such as NaBH$_4$, NaH or KH.

One can cite, as non-limiting examples, alkaline or alkaline-earth metal carbonates, such as cesium carbonate, an alkaline or alkaline-earth metal hydroxides, $C_{1-10}$ amidures, $C_{10-26}$ phosphazene or an alcoholate of formula (R$^{17}$O)$_2$M or R$^{17}$O M', wherein M is an alkaline-earth metal, M' is an alkaline metal or an ammonium NR$^{18}_4{}^+$, R$^{17}$ stands for hydrogen or a $C_1$ to $C_6$ linear or branched alkyl radical and R$^{18}$ stands for a $C_1$ to $C_{10}$ linear or branched alkyl radical, such as sodium, lithium, cesium or potassium alcoholates. Of course, other suitable bases can be used.

According to an embodiment of the invention, said base is an alkaline alcoholate of formula R$^{17}$OM'.

As previously mentioned the processes of the invention consist in the hydrogenation of a substrate using a ruthenium complex and a base. A typical process implies the mixture of the substrate with the ruthenium complex, a base and optionally a solvent, and then treating such a mixture with molecular hydrogen at a chosen pressure and temperature.

The complex of the invention, an essential parameter of the process, can be added to the reaction medium in a large range of concentrations. As non-limiting examples, one can cite as complex concentration values those ranging from 1 ppm to 50000 ppm, relative to the amount of substrate. Preferably, the complex concentration will be comprised between 10 and 20000 ppm. Even more preferably, the complex concentration will be comprised between 10 and 5000 ppm. It goes without saying that the optimum concentration of complex will depend, as the person skilled in the art knows, on the nature of the latter, on the nature of the substrate and on the pressure of $H_2$ used during the process, as well as the desired time of reaction.

Useful quantities of base, added to the reaction mixture, may be comprised in a relatively large range. One can cite, as non-limiting examples, ranges between 5 to 50000 molar equivalents, relative to the complex (e.g. base/com=5 to 50000), preferably 20 to 10000.

The hydrogenation reaction can be carried out in the presence or absence of a solvent. When a solvent is required or used for practical reasons, then any solvent current in hydrogenation reactions can be used for the purposes of the invention. Non-limiting examples include aromatic solvents such as toluene, chlorobenzene or xylene, hydrocarbon solvents such as hexane or cyclohexane, ethers such as tetrahydrofuran, methyltetrahydrofuran or MTBE, polar solvents such as primary or secondary alcohols such as isopropanol or ethanol, or mixtures thereof. The choice of the solvent is a function of the nature of the complex and the person skilled in the art is well able to select the solvent most convenient in each case to optimize the hydrogenation reaction.

In the hydrogenation process of the invention, the reaction can be carried out at a $H_2$ pressure comprised between $10^5$ Pa and $100 \times 10^5$ Pa (1 to 100 bars) or even more if desired. Again, a person skilled in the art is well able to adjust the pressure as a function of the catalyst load and of the dilution of the substrate in the solvent. As examples, one can cite typical pressures of 1 to $50 \times 10^5$ Pa (1 to 50 bars).

The temperature at which the hydrogenation can be carried out is comprised between 0° C. and 120° C., more preferably in the range of between 20° C. and 100° C. Of course, a person skilled in the art is also able to select the preferred temperature as a function of the melting and boiling point of the starting and final products as well as the desired time of reaction or conversion.

The ligand of formula (L) as defined above is also new. So another object of the present invention is the Ligand of formula (L).

In addition, the catalyst of the present invention is also novel. So a last object of the present invention is a ruthenium complex of the general formula (1) as defined above.

EXAMPLES

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out in open glass tubes placed inside a stainless steel autoclave. $H_2$ gas (99.99990%) was used as received. All substrates and solvents were distilled from appropriate drying agents under Ar. NMR spectra were recorded on a Bruker AM-400 ($^1H$ at 400.1 MHz, $^{13}C$ at 100.6 MHz, and $^{31}P$ at 161.9 MHz) spectrometer and normally measured at 300 K, in $CDCl_3$ unless indicated otherwise. Chemical shifts are listed in ppm.

Example 1

Preparation of Ligand of the Invention a) N-(2-(diphenylphosphino)benzyl)-1-(6-((diphenylphosphino)methyl)pyridin-2-yl)methanimine (L-1)

Preparation of 6-((diphenylphosphino)methyl)picolinaldehyde 6-((diphenylphosphino)methyl)picolinaldehyde was obtained according to some previously described procedure (Tan X., Wang Y., Liu Y., Wang F., Shi L., Lee K.-H., Lin Z., Lv H., Zhang X., *Org. Lett.,* 2015, 17 (3), 454-457). Initially isolated by filtration as the hydrochloride salt upon hydrolysis reaction of the acetal derivative under acidic aqueous conditions, basic treatment of the recovered white solid with sodium carbonate afforded desired product as a pale yellow solid.

$^1H$ NMR (500 MHz, CD2Cl2): δ (ppm) 3.71 (s, 2H, CH2), 7.17 (d, J=7.7 Hz, 1H, CH), 7.31 (m, 6H, 6CH), 7.44 (m, 4H, 4CH), 7.63 (t, J=7.7 Hz, 1H, CH), 7.68 (d, J=7.6 Hz, 1H, CH), 9.92 (s, 1H, CH).

$^{13}C$ NMR (125 MHz, CD2Cl2): δ (ppm) 38.7 (CH2), 119.2 (CH), 128.3 (CH), 128.8 (CH), 129.3 (CH), 133.3 (CH), 138.2 (C), 152.9 (C), 159.5 (C), 193.9 (CHO).

$^{31}P$ NMR (202 MHz, CD2Cl2): δ (ppm) −9.74 (s).

(2-(diphenylphosphino)phenyl)methanamine (2-(diphenylphosphino)phenyl)methanamine may be synthesized in 2 steps from 2-bromobenzonitrile according to the following pathway Step 1: Pd(PPh$_3$)$_4$ (0.8 mol. %), 2-bromobenzonitrile and degazed and dry toluene were loaded altogether in a round-bottomed flash equipped with a magnetic stirring bar and a dropping funnel. After purging with nitrogen, NEt$_3$ (1.04 eq.) was slowly added a room temperature. Upon addition completion, diphenylphosphine (1.03 eq.) was also slowly added a room temperature and reaction mixture was then heated to reflux for 12 h. After cooling down to room temperature, it was washed with degassed water, two times with 20 wt. % aqueous NH$_4$Cl to bring pH down to neutrality and then with water. After azetropic water removal, toluene was fully concentrated to afford crude product as a yellow-orange sticky solid. It was recrystallized from MeOH to afford desired 2-(diphenylphosphino)benzonitrile as a pale yellow solid in 80% yield.

2-(diphenylphosphino)benzonitrile $^1H$ NMR (400 MHz, CDCl3): δ (ppm) 7.04 (ddd, J=7.6, 4.5 and 1.1 Hz, 1H, CH), 7.27-7.34 (m, 7H, 7CH), 7.34-7.40 (m, 6H, 6CH), 7.42 (dd, J=7.6 and 1.1 Hz, 1H, CH), 7.47 (td, J=7.8 and 1.4 Hz, 1H, CH), 7.71 (ddd, J=7.8, 3.0 and 1.4 Hz, 1H, CH).

$^{13}C$ NMR (100 MHz, CDCl3): δ (ppm) 117.8 (C), 128.8 (CH), 128.9 (CH), 129.4 (CH), 132.4 (CH), 133.4 (CH), 133.7 (C), 133.9 (CH), 134.2 (CH), 134.7 (C), 143.2 (C).

$^{31}P$ NMR (162 MHz, CDCl3): δ (ppm) −7.79 (s, 1P).

Step 2: Degassed and dry THF was added under nitrogen to a round-bottomed flask equipped with a magnetic stirring bar and containing pre-weighted LiAlH4 (1.2 eq.). The suspension was cooled down to 0° C. and 2-(diphenylphosphino)benzonitrile was added portionwise. After 2 additional hours at 0° C. it was stirred at room temperature overnight. It was then cooled down back to 0° C. and slowly quenched with aqueous sodium hydroxide. After THF removal, the remaining residue was dissolved in DCM, passed through a celite plug. The DCM solution was washed with water, dried other sodium sulfate and concentrated to dryness and further dried under high vacuum to afford desired product as a pale yellow solid.

(2-(diphenylphosphino)phenyl)methanamine $^1$H NMR (400 MHz, CD2Cl2): δ (ppm) 1.35 (broad s, 2H, NH2), 3.97 (d, J=1.65 Hz, 2H, CH2), 6.87 (ddd, J=7.6, 4.5 and 1.2 Hz, 1H, CH), 7.12 (td, J=7.6 and 1.2 Hz, 1H, CH), 7.20-7.38 (m, 11H, 11CH), 7.42-7.48 (m, 1H, CH).

$^{13}$C NMR (100 MHz, CD2Cl2): δ (ppm) 45.4 (CH2), 127.3 (CH), 128.2 (CH), 128.9 (CH), 129.1 (CH), 129.6 (CH), 133.8 (CH), 134.2 (CH), 135.4 (C), 137.1 (C), 148.2 (C).

$^{31}$P NMR (162 MHz, CD2Cl2): δ (ppm) −15.55 (s, 1P).

(E)-N-(2-(diphenylphosphino)benzyl)-1-(6-((diphenylphosphino)methyl)pyridin-2-yl)methanimine (L-1)

(E)-N-(2-(diphenylphosphino)benzyl)-1-(6-((diphenylphosphino)methyl)pyridin-2-yl)methanimine was obtained by reaction at room temperature in THF of an equimolar mixture of 6-((diphenylphosphino)methyl)picolinaldehyde and ((2-(diphenylphosphino)phenyl)methanamine. Pure compound was obtained in quantitative yield as a pale yellow viscous oil upon solvent concentration and drying under high vacuum overnight.

$^1$H NMR (500 MHz, CD2Cl2): δ (ppm) 3.61 (s, 2H, CH2), 5.04 (broad s, 2H, CH2), 6.90-6.96 (m, 2H), 7.20-7.50 (m, 25H), 8.25 (s, 1H, CH imine).

$^{13}$C NMR (125 MHz, CD2Cl2): δ (ppm) 38.7 (CH2), 63.4 (CH2), 118.5 (CH), 124.9 (CH), 127.7 (CH), 128.7 (CH), 128.9 (CH), 129.0 (CH), 129.2 (CH), 129.5 (CH), 133.3 (CH), 134.0 (CH), 134.2 (CH), 134.4 (CH), 136.1 (C), 136.7 (CH), 137.1 (C), 138.7 (C), 144.1 (C), 154.7 (C), 158.1 (C), 163.7 (CH).

$^{31}$P NMR (202 MHz, CD2Cl2): δ (ppm) −15.33 (s, 1P), −10.47 (s, 1P).

b) Preparation of (E)-N-(2-(diphenylphosphino)benzyl)-1-(6-((di-tert-butylphosphino)methyl)pyridin-2-yl)methanimine (L-2)

Preparation of 6-((di-tert-butylphosphino)methyl)picolinaldehyde 6-((di-tert-butylphosphino)methyl)picolinaldehyde was obtained according to some similar multi-step synthesis as for 6-((diphenylphosphino)methyl)picolinaldehyde. It was fully characterized by 1H, 13C and 31P NMR analysis.

1H-NMR (300 MHz, CDCl3): δ 9.96 (1H, s, CHO), 7.71-7.65 (2H, m, 2×HPy), 7.62-7.58 (1H, m, HPy), 3.07 (2H, d, J=3.3 Hz, CH2P), 1.10 (18H, d, J=11.2 Hz, 6×CH3);

13C-NMR (75 MHz, CDCl3): δ 193.8 (CHO), 163.2 (d, J=14.7 Hz, CPy), 152.0 (CPy), 136.8 (CHPy), 128.3 (d, J=9.3 Hz, CHPy), 118.8 (d, J=1.3 Hz, CHPy), 32.0 (d, J=21.5 Hz, 2×CP), 31.5 (d, J=24.6 Hz, C H2P), 29.6 (d, J=13.3 Hz, 6×CH3);

31P-NMR (121 MHz, CDCl3): δ+37.7 s;

Preparation of (E)-N-(2-(diphenylphosphino)benzyl)-1-(6-((di-tert-butylphosphino)methyl)pyridin-2-yl)methanimine (L-2)

(E)-N-(2-(diphenylphosphino)benzyl)-1-(6-((di-tert-butylphosphino)methyl)pyridin-2-yl)methanimine was obtained by condensation at room temperature in THF of an equimolar mixture of 6-((di-tert-butylphosphino)methyl)picolinaldehyde and (2-(diphenylphosphino)phenyl)methanamine. It was obtained in quantitative yield as a pale yellow viscous oil upon solvent concentration and drying under high vacuum overnight and used directly for complex synthesis c) Preparation of (E)-N-(2-(diphenylphosphino)benzyl)-1-(6-((di-tert-butylphosphino)methyl)pyridin-2-yl) ethan-1-imine (L-3)

Preparation of 1-(6-((Di-tert-butylphosphino)methyl)pyridin-2-yl)ethan-1-one)

1-(6-((Di-tert-butylphosphino)methyl)pyridin-2-yl)ethan-1-one was obtained according to some procedure previously described in Angew. Chem. Int. Ed. 2016, 55, 6671-6675. It was fully characterized by 1H, 13C and 31P NMR analysis, with data corresponding the the previously reported ones.

Preparation of (E)-N-(2-(diphenylphosphino)benzyl)-1-(6-((di-tert-butylphosphino)methyl)pyridin-2-yl) ethan-1-imine (L-3)

E)-N-(2-(diphenylphosphino)benzyl)-1-(6-((di-tert-butylphosphino)methyl)pyridin-2-yl) ethan-1-imine was obtained by condensation at room temperature in THF of an equimolar mixture of 1-(6-((Di-tert-butylphosphino)methyl)pyridin-2-yl)ethan-1-one and (2-(diphenylphosphino)phenyl)methanamine. It was obtained in quantitative yield as a pale yellow solid upon solvent concentration and drying under high vacuum overnight and used directly for complex synthesis Example 2

Preparation of Invention Complex a) Preparation of [RuCl$_2$((E)-N-(2-(diphenylphosphino)benzyl)-1-(6-((diphenylphosphino)methyl)pyridin-2-yl)methanimine)] (Complex C1)

Complex C1 was obtained by reaction of (PPh$_3$)$_3$RuCl$_2$ ruthenium complex with 1.05 equivalents of ligand L1 in toluene refluxing for 4 h. Upon cooling down to room temperature, toluene was partly concentrated under vacuum and Et$_2$O was added for product precipitation. The suspension was filtered under nitrogen and the obtained purple solid was washed several times with a toluene/Et$_2$O mixture and then pure Et$_2$O. After drying under high vacuum overnight, product was obtained in 85% yield as a 5/2 stereoisomers mixture.

$^{31}$P NMR (202 MHz, CD2Cl2): δ (ppm) 46.27 (d, J=22.8 Hz, 1P major isomer), 47.34 (d, J=28.6 Hz, 1P minor isomer), 48.49 (d, J=22.8 Hz, 1P major isomer), 59.49 (d, J=28.6 Hz, 1P minor isomer).

b) Preparation of Complex [RuCl₂((E)-N-(2-(diphenylphosphino)benzyl)-1-(6-((di-tert-butylphosphino)methyl)pyridin-2-yl)methanimine)] (Complex C2)

Complex C2 was obtained by reaction of (PPh₃)₃RuCl₂ ruthenium complex with 1.05 equivalents of (E)-N-(2-(diphenylphosphino)benzyl)-1-(6-((di-tert-butylphosphino)methyl)pyridin-2-yl)methanimine (L-2) in toluene refluxing for 4 h. Upon cooling down to room temperature, toluene was partly concentrated under vacuum and Et₂O was added for product precipitation. The suspension was filtered under nitrogen and the obtained purple solid was washed several times with a toluene/Et₂O mixture and then pure Et₂O. After drying under high vacuum overnight, product was obtained in 75% yield as a 4/1 stereoisomers mixture.

³¹P NMR (202 MHz, CD₂Cl₂): δ 38.38 (d, J=18.5 Hz, 1P major isomer), 58.62 (broad s, 1P minor isomer), 61.82 (d, J=18.5 Hz, 1P major isomer), 62.35 (broad s, 1P minor isomer).

c) Preparation of Complex [RuCl₂((E)-N-(2-(diphenylphosphino)benzyl)-1-(6-((di-tert-butylphosphino)methyl)pyridin-2-yl)ethan-1-imine)] (Complex C3)

Complex C3 was obtained by reaction of (PPh₃)₃RuCl₂ ruthenium complex with 1.05 equivalents of (E)-N-(2-(diphenylphosphino)benzyl)-1-(6-((di-tert-butylphosphino)methyl)pyridin-2-yl)ethan-1-imine (L-3) in toluene refluxing for 4 h. Upon cooling down to room temperature, toluene was partly concentrated under vacuum and Et₂O was added for product precipitation. The suspension was filtered under nitrogen and the obtained purple solid was washed several times with a toluene/Et₂O mixture and then pure Et₂O. After drying under high vacuum overnight, product was obtained in 85% yield as a single isomer.

1H-NMR (500 MHz, CD2Cl2): δ 7.80-7.70 (m, 5H), 7.58 (t, J=1.80 Hz, 1H), 7.45-7.25 (m, 11H), 5.21 (t, J=3.2 Hz, 2H, CH2), 3.79 (d, J=8.8 Hz, 2H, CH2), 2.78 (s, 3H, CH3), 1.10 (s, 9H, 3 CH3), 1.07 (s, 9H, 3 CH3).

13C-NMR (125.76 MHz, CD2Cl2): δ 169.26 (C), 166.09 (C), 159.58 (C), 139.24 (C), 138.57 (C), 136.82 (C), 135.62 (CH), 135.10 (CH), 134.06 (CH), 132.09 (CH), 131.21 (CH), 129.78 (CH), 129.11 (CH), 128.88 (CH), 128.09 (CH), 128.00 (CH), 123.87 (CH), 122.47 (CH), 60.95 (CH2), 39.17 (CH2), 37.70 (C), 30.54 (CH3), 17.04 (CH3).

³¹P NMR (202 MHz, CD2Cl2): δ 35.84 (d, J=19.5 Hz, 1P), 63.47 (d, J=19.5 Hz, 1P).

Example 3

Preparation of Comparative Complexes a) Preparation of [RuCl₂(2-(diphenylphosphino)-N-((6-((diphenylphosphino)methyl)pyridin-2-yl)methyl)ethan-1-amine)] (Comparative Complex CC1)

Complex [RuCl₂(2-(diphenylphosphino)-N-((6-((diphenylphosphino)methyl)pyridin-2-yl)methyl)ethan-1-amine)] was obtained according to some previously described procedure (Tan X., Wang Y., Liu Y., Wang F., Shi L., Lee K.-H., Lin Z., Lv H., Zhang X., *Org. Lett.*, 2015, 17 (3), 454-457).

b) Preparation of [RuCl₂((E)-N-(2-(diphenylphosphino)ethyl)-1-(6-((diphenylphosphino)methyl)pyridin-2-yl)methanimine)] (comparative Complex CC2)

(E)-N-(2-(diphenylphosphino)ethyl)-1-(6-((diphenylphosphino)methyl)pyridin-2-yl)methanimine ligand (E)-N-(2-(diphenylphosphaneyl)ethyl)-1-(6-((diphenylphosphaneyl)methyl)pyridin-2-yl)methanimine (E)-N-(2-(diphenylphosphino)ethyl)-1-(6-((diphenylphosphino)methyl)pyridin-2-yl)methanimine ligand was obtained by reaction at room temperature in THF of an equimolar mixture of 6-((diphenylphosphino)methyl)picolinaldehyde and 2-(diphenylphosphino)ethan-1-amine Pure compound was obtained in quantitative yield as a pale yellow viscous oil upon solvent concentration and drying under high vacuum overnight.

¹H NMR (500 MHz, CD₂Cl₂): δ (ppm) 2.46 (tm, J=7.8 Hz, 2H, CH₂), 3.62 (s, 2H, CH₂), 3.75 (qm, J=7.8 Hz, 2H, CH₂) 6.94 (d, J=7.8 Hz, 1H, CH), 7.31 (m, 12H, 12CH), 7.44 (m, 9H, 9CH), 7.63 (d, J=7.8 Hz, 1H, CH), 8.22 (s, 1H, CH).

¹³C NMR (125 MHz, CD₂Cl₂): δ (ppm) 30.0 (CH₂), 38.7 (CH₂), 58.4 (CH₂), 118.5 (CH) 124.9 (CH), 128.7 (CH), 128.8 (CH), 128.9 (CH), 129.1 (CH) 133.1 (CH), 133.2 (CH), 136.8 (CH), 138.8 (C), 138.9 (C), 154.6 (C), 158.2 (C), 162.8 (CH).

³¹P NMR (202 MHz, CD₂Cl₂): δ (ppm) −18.73 (s), −10.41 (s).

[RuCl₂((E)-N-(2-(diphenylphosphino)ethyl)-1-(6-((diphenylphosphino)methyl)pyridin-2-yl)methanimine)] (Complex CC2)

it was obtained by reaction of (PPh₃)₃RuCl₂ ruthenium complex with 1.05 equivalents of (E)-N-(2-(diphenylphosphino)ethyl)-1-(6-((diphenylphosphino)methyl)pyridin-2-yl)methanimine ligand in toluene refluxing for 4 h. Upon cooling down to room temperature, toluene was partly concentrated under vacuum and Et₂O was added for product precipitation. The suspension was filtered under nitrogen and the obtained purple solid was washed several times with a toluene/Et₂O mixture and then pure Et₂O. After drying under high vacuum overnight, pure product was obtained in 85% yield.

¹H NMR (500 MHz, CD₂Cl₂): δ (ppm) 3.21 (qm, J=7.8 Hz, 2H, CH₂), 4.52 (d, J=10.4 Hz, 2H, CH₂), 4.60-4.70 (m, 2H, CH₂), 7.22-7.28 (m, 8H, 8CH), 7.30-7.38 (m, 4H, 4CH), 7.43-7.57 (m, 8H, 8CH), 7.74-7.86 (m, 3H, 3CH), 8.95 (dt, J=7.0 and 1.6 Hz, 1H, CH).

¹³C NMR (125 MHz, CD₂Cl₂): δ (ppm) 35.8 (CH₂), 47.7 (CH₂), 58.6 (CH₂), 122.5 (CH), 125.4 (CH), 127.8 (CH), 127.9 (CH), 129.6 (CH), 129.8 (CH), 133.8 (CH), 134.1 (CH), 135.0 (CH), 135.6 (C), 136.2 (C), 158.4 (C), 160.8 (CH) 162.5 (C).

³¹P NMR (202 MHz, CD₂Cl₂): δ (ppm) 54.6 (d, J=19.60 Hz), 60.5 (d, J=19.60 Hz)

c) Preparation of [RuCl2((E)-1-(6-((diphenylphosphino)methyl)pyridin-2-yl)-N-(3-(diphenylphosphino)propyl)methanimine)] (Comparative Complex CC3)

(E)-1-(6-((diphenylphosphino)methyl)pyridin-2-yl)-N-(3-(diphenylphosphino)propyl) methanimine ligand it was obtained by reaction at room temperature in THF of an equimolar mixture of 6-((diphenylphosphino)methyl)picolinaldehyde and 3-(diphenylphosphino)propan-1-amine Pure compound was obtained in quantitative yield as a pale yellow viscous oil upon solvent concentration and drying under high vacuum overnight.

$^1$H NMR (500 MHz, CD$_2$Cl$_2$): δ (ppm) 1.75-1.87 (m, 2H, CH$_2$), 2.09-2.16 (m, 2H, CH$_2$), 3.62 (s, 2H, CH$_2$), 3.70 (td, J=6.8 and 1.2 Hz, 2H, CH$_2$) 6.94 (dt, J=7.8 and 1.2 Hz, 1H, CH), 7.27-7.35 (m, 12H, 12CH), 7.38-7.46 (m, 8H, 8CH), 7.50 (t, J=7.8 Hz, 1H, CH), 7.63 (d, J=7.8 Hz, 1H, CH), 8.26 (s, 1H, CH).

$^{13}$C NMR (125 MHz, CD$_2$Cl$_2$): δ (ppm) 25.8 (CH$_2$), 27.7 (CH$_2$), 38.7 (CH$_2$), 62.4 (CH$_2$), 118.4 (CH) 124.9 (CH), 128.7 (CH), 128.9 (CH), 129.1 (CH) 133.0 (CH), 133.2 (CH), 136.8 (CH), 138.7 (C), 139.3 (C), 154.8 (C), 158.2 (C), 162.8 (CH).

$^{31}$P NMR (202 MHz, CD$_2$Cl$_2$): δ (ppm) −16.11 (s), −10.42 (s).

[RuCl2((E)-1-(6-((diphenylphosphino)methyl)pyridin-2-yl)-N-(3-(diphenylphosphino)propyl)methanimine)] (Comparative Complex CC3)

it was obtained by reaction of (PPh$_3$)$_3$RuCl$_2$ ruthenium complex with 1.05 equivalents of (E)-1-(6-((diphenylphosphino)methyl)pyridin-2-yl)-N-(3 (diphenylphosphino)propyl) methanimine ligand in toluene refluxing for 4 h. Upon cooling down to room temperature, toluene was partly concentrated under vacuum and Et$_2$O was added for product precipitation. The suspension was filtered under nitrogen and the obtained purple solid was washed several times with a toluene/Et$_2$O mixture and then pure Et$_2$O. After drying under high vacuum overnight, pure product was obtained in 75% yield.

$^1$H NMR (500 MHz, CD$_2$Cl$_2$): δ (ppm) 2.40-2.54 (m, 2H, CH$_2$), 2.79-2.87 (m, 2H, CH$_2$), 4.35-4.40 (m, 2H, CH$_2$), 4.41 (d, J=10.8 Hz, 2H, CH$_2$), 7.08-7.14 (m, 8H, 8CH), 7.16-7.22 (m, 4H, 4CH), 7.23-7.30 (m, 4H, 4CH), 7.32-7.38 (m, 4H, 4CH), 7.61-7.67 (m, 1H, CH, 7.75-7.81 (m, 2H, 2CH), 8.71 (dt, J=5.8 and 1.8 Hz, 1H, CH).

$^{13}$C NMR (125 MHz, CD$_2$Cl$_2$): δ (ppm) 24.4 (CH$_2$), 27.5 (CH$_2$), 48.7 (CH$_2$), 63.0 (CH$_2$), 122.7 (CH) 125.4 (CH), 127.5 (CH), 127.6 (CH), 129.1 (CH), 129.6 (CH), 134.1 (CH), 134.2 (CH), 135.4 (CH), 135.8 (C), 138.0 (C), 155.6 (C), 162.4 (C), 165.0 (CH).

$^{31}$P NMR (202 MHz, CD$_2$Cl$_2$): δ (ppm) 36.12 (d, J=30.4 Hz), 50.5 (d, J=30.4 Hz).

d) [RuCl2(triphenylphosphine)(bis(2-(ethylthio)ethyl)amine)] (Comparative Complex CC4)

Commercially available complex [RuCl2(triphenylphosphine)(bis(2-(ethylthio)ethyl)amine)] was purchased from Sigma-Aldrich.

e) [RuCl2(N,N'-(ethane-1,2-diyl)bis(1-(2-(diphenylphosphaneyl)phenyl)methanimine))] (Comparative Complex CC5)

Complex [RuCl2(N,N'-(ethane-1,2-diyl)bis(1-(2-(diphenylphosphaneyl)phenyl)methanimine))] was synthesized according to some previously described procedure (Saudan L., Dupau P., Riedhauser J.-J., Wyss P., WO200610648)

f) [RuCl2(bis(2-(diphenylphosphino)ethylamine))] (Comparative Complex CC6)

Commercially available complex [RuCl2(bis(2-(diphenylphosphino)ethylamine))] was purchased from Sigma-Aldrich (CAS number: [506417-41-0]).

Example 4

General Hydrogenation Reaction Procedure:

Ester, ruthenium catalyst, metal alkoxide co-catalyst (used as a solid or some alcoholic solution) and optionally solvent (see Table 1) were loaded altogether in an 100 mL or 1 L autoclave equipped with a mechanical stirring device, pressure and internal temperature sensors and a heating/cooling system for internal temperature regulation. Sealed autoclave was then purged under stirring with nitrogen (3 times 5 bars) and hydrogen (3 times 5 bars) before being pressurized to required hydrogen pressure via an hydrogen tank equipped with a way out pressure regulator and also an internal pressure sensor to follow and determine hydrogen consumption. Reaction mixture was then heated to required temperature and hydrogen pressure into the autoclave was maintained to the desired value during the whole reaction. Upon reaction completion also determined by GC analysis with complete disappearance of both starting material and mixed ester coming from transesterification reaction with product and eventually with metal alkoxide co-catalyst and/or alcoholic solvent, autoclave was then cooled down to 25° C. It was then depressurized and purged with nitrogen (3 times 5 bars) and reaction mixture was then transferred to a round-bottomed flask and lights compounds were removed under vacuum. Crude product was then flash distilled in order to determine the quantity of residues formed during the reaction and yield was calculated based on GC purity of distilled product.

Example 5

Catalytic hydrogenation of different esters using different catalyst of the invention and comparative catalyst:

The hydrogenation has been performed as reported in Example 4.

TABLE 1

Hydrogenation of different esters using different complexes

| Entry | Ester | Complex (mol %) | NaOEt (mol %) | P (bars) | T (° C.) | Time for complete Conversion [1] (h) | Yield |
|---|---|---|---|---|---|---|---|
| 1 | E1 | CC1 (0.00166) | 5 | 50 | 100 | 7 | >99% |
| 2 | E1 | CC2 (0.00166) | 5 | 50 | 100 | 7 | >99% |
| 3 | E1 | CC3 (0.00166) | 5 | 50 | 100 | 7 | >99% |
| 4 | E1 | C1 (0.00166) | 5 | 50 | 100 | 1 | >99% |
| 5 | E2 | CC1 (0.00166) | 5 | 50 | 100 | 4 | >99% |
| 6 | E2 | CC2 (0.00166) | 5 | 50 | 100 | 4 | >99% |
| 7 | E2 | C1 (0.00166) | 5 | 50 | 100 | 1.5 | >99% |
| 8 | E3 | CC1 (0.00333) | 5 | 50 | 100 | 3 | >98% [2] |
| 9 | E3 | CC2 (0.00333) | 5 | 50 | 100 | 3 | >98% [2] |
| 10 | E3 | C1 (0.00333) | 5 | 50 | 100 | 1 | >98% [2] |
| 11 | E2 | C1 (0.01) | 5 | 50 | 80 | 0.66 | >99% |
| 12 | E2 | C2 (0.01) | 5 | 50 | 80 | 0.8 | >99% |

TABLE 1-continued

Hydrogenation of different esters using different complexes

| Entry | Ester | Complex (mol %) | NaOEt (mol %) | P (bars) | T (° C.) | Time for complete Conversion [1] (h) | Yield |
|---|---|---|---|---|---|---|---|
| 13 | E2 | C3 (0.01) | 5 | 50 | 80 | 1 | >99% |
| 14 | E2 | CC1 (0.01) | 5 | 50 | 80 | 2.5 | >99% |
| 15 | E2 | CC4 (0.01) | 5 | 50 | 80 | 5 | >99% |
| 16 | E2 | CC5 (0.01) | 5 | 50 | 80 | 24 | >99% |
| 17 | E2 | CC6 (0.01) | 5 | 50 | 80 | >36 | n.d. |

[1] Complete conversion was achieved with nearly no residues formation (<1 wt. %).
[2] Product was obtained with >99% GC selectivity The complete conversion was reached faster with the invention's catalyst compared to prior art catalysts.

TABLE 2

Structure and names of esters used

| Ester | Structure | Name |
|---|---|---|
| E1 | 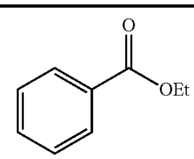 | Ethyl benzoate |
| E2 | 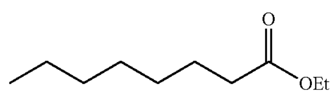 | Ethyl octanoate |
| E3 | 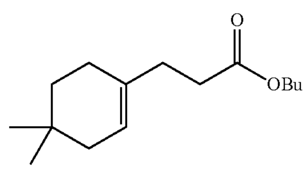 | Butyl 3-(4,4-dimethylcyclohex-1-en-1-yl)propanoate |
| E4 | 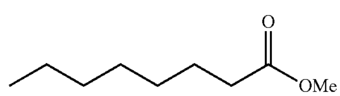 | Methyl octanoate |
| E5 | 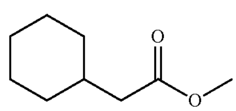 | Methyl 2-cyclohexylacetate |
| E6 | 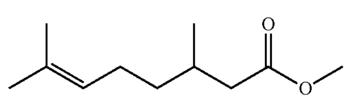 | Methyl 3,7-dimethyloct-6-enoate |
| E7 | 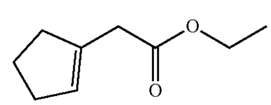 | Ethyl 2-(cyclopent-1-en-1-yl)acetate |
| E8 | 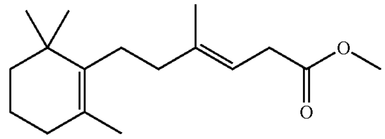 [SMILES: COC(=O)C/C=C(\C)CCC1=C(C)CCCC1(C)C] | Methyl (E)-4-methyl-6-(2,6,6-trimethylcyclohex-1-en-1-yl)hex-3-enoate |
| E9 | 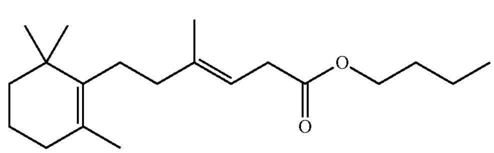 [SMILES: CCCCOC(=O)C/C=C(\C)CCC1=C(C)CCCC1(C)C] | Butyl (E)-4-methyl-6-(2,6,6-trimethylcyclohex-1-en-1-yl)hex-3-enoate |

TABLE 2-continued

Structure and names of esters used

| Ester | Structure | Name |
|---|---|---|
| E10 | 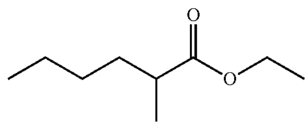 | Ethyl 2-methylhexanoate |
| E11 | 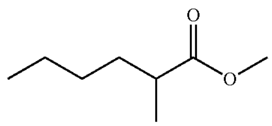 | Methyl 2-methylhexanoate |
| E12 | 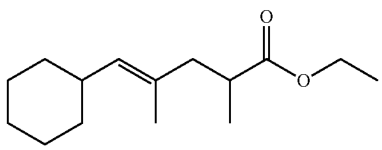 [SMILES: CCOC(=O)C(C)C/C(C)=C/C1CCCCC1] | Ethyl (E)-5-cyclohexyl-2,4-dimethylpent-4-enoate |
| E13 | 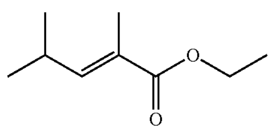 | Ethyl (E)-2,4-dimethylpent-2-enoate |
| E14 | 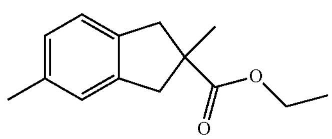 [SMILES: CCOC(=O)C1(C)Cc2ccc(C)cc2C1] | Ethyl 2,5-dimethyl-2,3-dihydro-1H-indene-2-carboxylate |
| E15 | 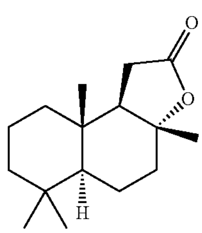 [SMILES: CC1(C)CCC[C@]2(C)[C@H]3CC(=O)O[C@]3(C)CC[C@@H]12] | (+/−)-(3aR,5aS,9aS,9bR)-3a,6,6,9a-tetramethyldecahydronaphtho[2,1-b]furan-2(1H)-one (racemic compound with displayed relative stereochemistry) |
| E16 | 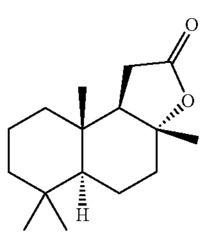 [SMILES: CC1(C)CCC[C@]2(C)[C@H]3CC(=O)O[C@]3(C)CC[C@@H]12] | (+)-(3aR,5aS,9aS,9bR)-3a,6,6,9a-tetramethyldecahydronaphtho[2,1-b]furan-2(1H)-one (enantiomerically enriched) |

Example 6

Catalytic Hydrogenation of Ethyl Benzoate Using Different Catalysts of the Invention and Comparative Catalysts in Various Solvents:

The hydrogenation has been performed as reported in Example 4.

TABLE 3

Hydrogenation of Ethyl benzoate using different complexes in various solvents

| Entry | Solvent[1] | Complex (mol %) | NaOEt (mol %) | P (bars) | T (° C.) | Time for complete Conversion [2] (h) | Yield |
|---|---|---|---|---|---|---|---|
| 1 | none | CC1 (0.00333) | 5 | 50 | 100 | 2 | >99% |
| 2 | none | CC2 (0.00333) | 5 | 50 | 100 | 2 | >99% |
| 3 | none | C1 (0.00333) | 5 | 50 | 100 | 0.5 | >99% |
| 4 | iPrOH | CC1 (0.00333) | 5 | 50 | 100 | 4 | >99% |
| 5 | iPrOH | CC2 (0.00333) | 5 | 50 | 100 | 4 | >99% |
| 6 | iPrOH | C1 (0.00333) | 5 | 50 | 100 | 1 | >99% |
| 7 | EtOH | CC1 (0.00333) | 5 | 50 | 100 | 4 | >99% |
| 8 | EtOH | CC2 (0.00333) | 5 | 50 | 100 | 4 | >99% |
| 9 | EtOH | C1 (0.00333) | 5 | 50 | 100 | 1 | >99% |
| 10 | THF | CC1 (0.00333) | 5 | 50 | 100 | 5 | >99% |
| 11 | THF | CC2 (0.00333) | 5 | 50 | 100 | 5 | >99% |
| 12 | THF | C1 (0.00333) | 5 | 50 | 100 | 1.5 | >99% |
| 13 | Toluene | CC1 (0.00333) | 5 | 50 | 100 | 8 | >99% |
| 14 | Toluene | CC2 (0.00333) | 5 | 50 | 100 | 8 | >99% |
| 15 | Toluene | C1 (0.00333) | 5 | 50 | 100 | 1.5 | >99% |
| 16 | Chlorobenzene | CC1 (0.00333) | 5 | 50 | 100 | 6 | >99% |
| 17 | Chlorobenzene | CC2 (0.00333) | 5 | 50 | 100 | 6 | >99% |
| 18 | chlorobenzene | C1 (0.00333) | 5 | 50 | 100 | 1.5 | >99% |

[1] Reactions were run (when applicable) with 2 equivalents in volume of solvent.
[2] Complete conversion was achieved with nearly no residues formation (<1 wt. %).

The invention's catalyst allows reaching complete conversion faster than the prior art catalyst regardless of the solvent used.

Example 7

Catalytic Hydrogenation of Different Esters Using Complex C1 at Various Temperatures:

The hydrogenation has been performed as reported in Example 4.

TABLE 4

Hydrogenation of ester using complex C1 at various temperature

| Entry | Ester | Complex (mol %) | NaOEt (mol %) | P (bars) | T (° C.) | Time for complete Conversion [1] (h) | Yield |
|---|---|---|---|---|---|---|---|
| 1 | E1 | C1 (0.01) | 5 | 50 | 40 | 4 | >99% |
| 2 | E1 | C1 (0.01) | 5 | 50 | 60 | 1 | >99% |
| 3 | E1 | C1 (0.003333) | 5 | 50 | 60 | 3 | >99% |
| 4 | E1 | C1 (0.003333) | 5 | 50 | 80 | 1 | >99% |
| 5 | E1 | C1 (0.001666) | 5 | 50 | 80 | 4 | >99% |
| 6 | E1 | C1 (0.001666) | 5 | 50 | 100 | 1 | >99% |
| 7 | E2 | C1 (0.01) | 5 | 50 | 40 | 12 | >99% |

TABLE 4-continued

Hydrogenation of ester using complex C1 at various temperature

| Entry | Ester | Complex (mol %) | NaOEt (mol %) | P (bars) | T (° C.) | Time for complete Conversion [1] (h) | Yield |
|---|---|---|---|---|---|---|---|
| 8 | E2 | C1 (0.01) | 5 | 50 | 60 | 2 | >99% |
| 9 | E2 | C1 (0.003333) | 5 | 50 | 60 | 6 | >99% |
| 10 | E2 | C1 (0.003333) | 5 | 50 | 80 | 2 | >99% |
| 11 | E2 | C1 (0.001666) | 5 | 50 | 80 | 6 | >99% |
| 12 | E2 | C1 (0.001666) | 5 | 50 | 100 | 1.5 | >99% |

[1] Complete conversion was achieved with nearly no residues formation (<1 wt. %).

Example 8

Catalytic Hydrogenation Under Neat Conditions of Ethyl Octanoate Using Complex C1 at Various Hydrogen Pressures:

The hydrogenation has been performed as reported in Example 4.

TABLE 5

Hydrogenation of ethyl octanoate with C1 at various hydrogen pressures

| Entry | Ester | Complex (mol %) | NaOEt (mol %) | P (bars) | T (° C.) | Time for complete Conversion [1] (h) | Yield |
|---|---|---|---|---|---|---|---|
| 1 | E2 | C1 (0.01) | 5 | 10 | 80 | 9 | >99% |
| 2 | E2 | C1 (0.01) | 5 | 20 | 80 | 3 | >99% |
| 3 | E2 | C1 (0.01) | 5 | 30 | 80 | 2 | >99% |
| 4 | E2 | C1 (0.01) | 5 | 50 | 80 | 0.66 | >99% |

[1] Complete conversion was achieved with nearly no residues formation (<1 wt. %).

Example 9

Catalytic Hydrogenation Under Neat Conditions of Ethyl Octanoate Using Complex C1 with Various Metal Alkoxides as a Base:

The hydrogenation has been performed as reported in Example 4.

TABLE 6

Neat hydrogenation using various metal alkoxides as a base

| Entry | Ester | Complex (mol %) | Base (mol %) | P (bars) | T (° C.) | Time for complete Conversion [1] (h) | Yield |
|---|---|---|---|---|---|---|---|
| 1 | E2 | C1 (0.003333) | NaOEt (5) | 50 | 80 | 2 | >99% |
| 2 | E2 | C1 (0.003333) | KOEt (5) | 50 | 80 | 5 | >99% |
| 3 | E2 | C1 (0.003333) | KO$^t$Bu (5) | 50 | 80 | 5 | >99% |
| 4 | E2 | C1 (0.003333) | LiOEt (5) | 50 | 80 | 12 | >99% |
| 5 | E2 | C1 (0.003333) | LiO$^t$Bu (5) | 50 | 80 | 12 | >99% |

[1] Complete conversion was achieved with nearly no residues formation (<1 wt. %).

Example 10

Catalytic Hydrogenation Under Neat Conditions of Various Esters Using Complex C1:

The hydrogenation has been performed as reported in Example 4.

TABLE 7

Neat hydrogenation of various esters

| Entry | Ester | Complex (mol %) | NaOEt (mol %) | P (bars) | T (° C.) | Time for complete Conversion [1] (h) | Yield |
|---|---|---|---|---|---|---|---|
| 1 | E4 | C1 (0.003333) | 7.5 | 50 | 80 | 12 | >99% |
| 2 | E5 | C1 (0.01) | 5 | 50 | 80 | 4 | >99% |
| 3 | E6 | C1 (0.01) | 5 | 50 | 80 | 5 | >98% [2] |
| 4 | E7 | C1 (0.005) | 5 | 50 | 80 | 2 | >98% [2] |
| 5 | E8 | C1 (0.005) | 2.5 | 50 | 80 | 9 | 94% [3] |
| 6 | E9 | C1 (0.01) | 2.5 | 50 | 80 | 4 | 94% [3] |
| 7 | E10 | C1 (0.01) | 5 | 50 | 80 | 5 | >99% |

TABLE 7-continued

Neat hydrogenation of various esters

| Entry | Ester | Complex (mol %) | NaOEt (mol %) | P (bars) | T (° C.) | Time for complete Conversion [1] (h) | Yield |
|---|---|---|---|---|---|---|---|
| 8 | E11 | C1 (0.01) | 5 | 50 | 80 | 16 | >99% |
| 9 | E12 | C1 (0.005) | 5 | 50 | 100 | 6 | >98% [2] |
| 10 | E13 | C1 (0.01) | 5 | 50 | 80 | 4 | 94% [3] |
| 11 | E14 | C1 (0.005) | 5 | 50 | 100 | 3 | >99% |

[1] Complete conversion was achieved with nearly no residues formation (<1 wt. %).
[2] Desired product was obtained with more than 99% GC selectivity at complete conversion.
[3] Desired product was obtained with 95% GC selectivity at complete conversion.

Example 11

Catalytic Hydrogenation of (+/−)-(3aR,5aS,9aS,9bR)-3a,6,6,9a-tetramethyldecahydronaphtho[2,1-b]furan-2(1H)-one Using Different Catalyst of the Invention and Comparative Catalyst in Various Solvents The hydrogenation has been performed as reported in Example 4.

TABLE 8

Neat Hydrogenation of (+/−)-(3aR,5aS,9aS,9bR)-3a,6,6,9a-tetramethyldecahydronaphtho[2,1-b]furan-2(1H)-one in solvent

| Entry | Solvent | Complex (mol %) | NaOEt (mol %) | P (bars) | T (° C.) | Time for complete Conversion [3] (h) | Yield |
|---|---|---|---|---|---|---|---|
| 1 | iPrOH [1] | C1 (0.0025) | 5 | 50 | 100 | 2 | >98% |
| 2 | iPrOH [1] | CC6 (0.01) | 5 | 50 | 100 | 24 | >98% |
| 3 | Chlorobenzene [2] | C1 (0.005) | 5 | 30 | 100 | 6 | >98% |
| 4 | chlorobenzene [2] | CC6 (0.04) | 5 | 30 | 100 | 24 | >98% |

[1] Reactions run with 1 equivalent in volume of solvent.
[2] Reactions run with 2 equivalents in volume of solvent.
[3] Complete conversion was achieved with nearly no residues formation (<1 wt. %).

Same results were obtained from enantiomerically enriched compound E16.

The invention claimed is:

1. A process for the reduction by hydrogenation, using molecular $H_2$, of a $C_3$-$C_{70}$ substrate containing one or two ketones, aldehydes, esters, or lactones functional groups into the corresponding alcohol, or diol, wherein said process is carried out in the presence of a base and at least one catalyst or pre-catalyst containing Ruthenium and a tetradentate ligand of formula

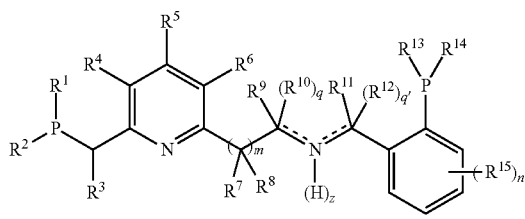

(L)

wherein one dotted line indicates a single bond and the other dotted line a single or a double bond, z is 1 when both dotted lines is a single bond or is 0 when one dotted line is a double bond and the other a single bond;

m is 0 or 1;

n is a integer between 0 and 4;

q is 0 when the dotted line between N and C(R$^9$)(R$^{10}$) indicates a double bond or is 1 when the dotted line between N and C(R$^9$)(R$^{10}$) indicates a single bond;

q' is 0 when the dotted line between N and C(R$^{11}$)(R$^{12}$) indicates a double bond or is 1 when the dotted line between N and C(R$^{11}$)(R$^{12}$) indicates a single bond;

R$^1$ and R$^2$, when taken separately, represent, simultaneously or independently, a linear $C_1$ to $C_8$ alkyl group optionally substituted, a linear $C_2$ to $C_8$ alkenyl group optionally substituted, a branched or cyclic $C_3$ to $C_8$ alkyl or alkenyl group optionally substituted, a $C_6$ to $C_{10}$ aromatic group optionally substituted, or an OR$^{1'}$ or NR$^{1'}$R$^{2'}$ group, R$^{1'}$ and R$^{2'}$ being a $C_1$ to $C_8$ alkyl group or a $C_2$ to $C_8$ alkenyl group; or R$^1$ and R$^2$, when taken together, form a saturated or unsaturated ring optionally substituted, having 4 to 10 atoms and including the phosphorus atom to which said R$^1$ and R$^2$ groups are bonded;

R$^3$, R$^4$, R$^5$, R$^6$, R$^7$, R$^8$, R$^9$, R$^{10}$, R$^{11}$ and R$^{12}$, taken separately, represent, simultaneously or independently, a hydrogen atom, a $C_1$-$C_{10}$ linear alkyl group optionally substituted, a $C_2$-$C_{10}$ linear alkenyl group optionally substituted, a $C_3$-$C_{10}$ branched or cyclic alkyl or alkenyl group optionally substituted or a $C_6$ to $C_{10}$ aromatic group optionally substituted; or R$^3$ and R$^4$ and/or R$^4$ and R$^5$ and/or R$^5$ and R$^6$ and/or R$^6$ and R$^7$ and/or R$^7$ and R$^8$ and/or R$^8$ and R$^9$ and/or R$^9$ and R$^{10}$ and/or R$^9$ and R$^{11}$ and/or R$^{11}$ and R$^{12}$, when taken together, form a saturated or unsaturated ring optionally substituted, having 4 to 10 atoms;

R$^{13}$ and R$^{14}$, when taken separately, represent, simultaneously or independently, a $C_6$ to $C_{10}$ aromatic group optionally substituted or an OR$^{1'}$ or NR$^{1'}$R$^{2'}$ group wherein R$^{1'}$ and R$^{2'}$ is a $C_1$ to $C_8$ alkyl group or a $C_2$ to $C_8$ alkenyl group; and R$^{15}$ when taken separately, represent, simultaneously or independently, a hydrogen atom, a halogen atom, a linear $C_1$ to $C_8$ alkyl group optionally substituted, a linear $C_2$ to $C_8$ alkenyl group optionally substituted, a branched or cyclic $C_3$ to $C_8$ alkyl or alkenyl group optionally substituted, or a halo- or perhalo-hydrocarbon, CN, SO$_3$R$^{3'}$, SO$_2$R$^{3'}$, NO$_2$, OR$^{3'}$, or CONR$^{3'}$R$^{4'}$ group, R$^{3'}$ and R$^{4'}$, independently from each other, being a hydrogen atom or a $C_1$ to $C_8$ alkyl group or a $C_2$ to $C_8$ alkenyl group; two adjacent R$^{15}$ groups can be bonded together to form a $C_5$ to $C_{10}$ ring optionally substituted;

the optional substituents of the R$^1$ to R$^{15}$ groups are one or two halogen atoms, $C_1$ to $C_{10}$ alkoxy, polyalkyleneglycols, halo- or perhalo-hydrocarbon, COOR, or R groups, wherein R is a $C_1$ to $C_6$ alkyl, or a $C_5$ to $C_{12}$ cycloalkyl, aralkyl or aromatic group, the latter being also optionally substituted by one, two, or three halogen atoms or $C_1$-$C_8$ alkyl, alkoxy, nitro, sulfonates, halo- or perhalo-hydrocarbon or ester groups.

2. A process according to claim 1, wherein the ruthenium complex is of formula $$[Ru(L)Y_2] \qquad (1)$$

wherein L represents a tetradentate ligand as defined in claim 1; and each Y represents, simultaneously or independently, CO, a hydrogen or halogen atom, a hydroxyl group, or a $C_1$-$C_6$ alkyl, alkenyl, alkoxy, or carboxylic radical, or a BH$_4$ or ALH$_4$ group.

3. A process according to claim 1, wherein m is 1.

4. A process according to claim 1, wherein L is a ligand of formula

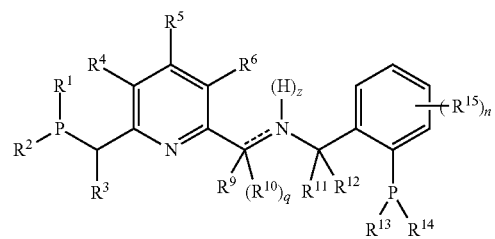

(L2)

wherein z, n, q, R$^1$, R$^2$, R$^3$, R$^4$, R$^5$, R$^6$, R$^9$, R$^{10}$, R$^{11}$, R$^{12}$, R$^{13}$, R$^{14}$, and R$^{15}$ have the same meaning as defined in claim 1.

5. A process according to claim 1, wherein R$^1$ and R$^2$ represent, simultaneously or independently, a linear $C_1$ to $C_6$ alkyl group optionally substituted, a branched or cyclic $C_3$ to $C_6$ alkyl group optionally substituted, a phenyl group optionally substituted; or R$^1$ and R$^2$, when taken together, form a saturated or unsaturated ring optionally substituted, having 4, 5, 6, or 7 carbon atoms and including the phosphorus atom to which said R$^1$ and R$^2$ groups are bonded.

6. A process according to claim 5, wherein R$^1$ and R$^2$ represent a cyclohexyl, a phenyl, a tert-butyl, an iso-propyl, or an ethyl group.

7. A process according to claim 1, wherein R$^{13}$ and R$^{14}$ represent a phenyl group optionally substituted.

8. A process according to claim 1, wherein R$^3$, R$^4$, R$^5$, R$^6$, R$^7$, R$^8$, R$^9$, R$^{10}$, R$^{11}$, and R$^{12}$, taken separately, represent, simultaneously or independently, a hydrogen atom, a $C_1$-$C_4$ linear alkyl group optionally substituted, a $C_5$-$C_6$ branched or cyclic alkyl group optionally substituted or a phenyl group optionally substituted; R$^4$ and R$^5$ or R$^5$ and R$^6$ or R$^8$ and R$^9$, when taken together, form a saturated or unsaturated ring optionally substituted, having 4 to 7 carbon atoms.

9. A process according to claim 1, wherein L is a ligand of formula

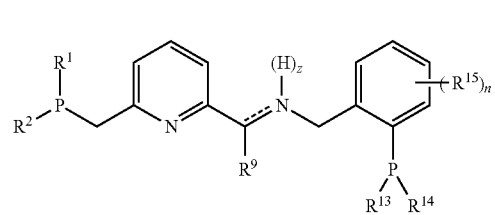

(L3)

wherein z, n, R$^1$, R$^2$, R$^9$, R$^{13}$, R$^{14}$, and R$^{15}$ have the same meaning as defined in claims 1 to 8.

10. A process according to claim 1, wherein the base has a pK$_a$ above 14.

11. A process according to claim 10, wherein the base is an alkaline or alkaline-earth metal carbonates, an alkaline or alkaline-earth metal hydroxides, $C_{1-10}$ amidures, $C_{10-26}$ phosphazene, or an alcoholate of formula (R$^{17}$O)$_2$M or $R^{17}OM'$, wherein M is an alkaline-earth metal, M' is an alkaline metal or an ammonium $NR^{18}_4{}^+$, wherein $R^{17}$ stands for hydrogen or a $C_1$ to $C_6$ linear or branched alkyl radical and $R^{18}$ stands for a $C_1$ to $C_{10}$ linear or branched alkyl radical.

12. A process according to claim 1, wherein the substrate is a compound of formula (I)

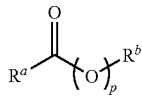
(I)

wherein p is 0 or 1;

when p is 1, $R^a$ and $R^b$ represent, simultaneously or independently, a linear, branched or cyclic $C_1$-$C_{30}$ aromatic, alkyl, or alkenyl group, optionally substituted; or when p is 0, $R^a$ represents a linear, branched or cyclic $C_1$-$C_{30}$ aromatic, alkyl, or alkenyl group, optionally substituted and $R^b$ represents a hydrogen atom, a linear, branched or cyclic $C_1$-$C_{30}$ aromatic, alkyl, or alkenyl group, optionally substituted; or $R^a$ and $R^b$ are bonded together and form a $C_4$-$C_{20}$ saturated or unsaturated group, optionally substituted; and wherein the substituents of $R^a$ and $R^b$ are a $COOR^c$, group, one, two, or three halogen, $OR^c$, $NR^c_2$ or $R^c$ groups, in which $R^c$ is a hydrogen atom, a halogenated $C_1$-$C_2$ group, or a $C_1$ to $C_{10}$ cyclic, linear or branched alkyl, or alkenyl group.

13. A process according to claim 12, wherein the substrate is a $C_5$-$C_{30}$ compound of formula (I) wherein $R^a$ and $R^b$ represent, simultaneously or independently, a linear $C_1$-$C_{30}$ alkyl group optionally substituted, a branched or cyclic $C_3$-$C_{30}$ alkyl or alkenyl group optionally substituted, or a $C_5$-$C_{30}$ aromatic group optionally substituted; or $R^a$ and $R^b$ are bonded together and form a $C_4$-$C_{20}$ saturated or unsaturated linear, branched, mono-, di-, or tri-cyclic group, optionally substituted.

14. A ligand of formula

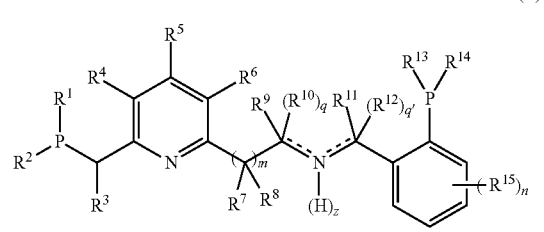
(L)

wherein m, n, q, q' z, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ have the same meaning as in any one of claim 1 to 9.

15. A complex of formula (1), as defined in claim 2.

* * * * *